US009505789B2

(12) United States Patent
Hoye et al.

(10) Patent No.: US 9,505,789 B2
(45) Date of Patent: Nov. 29, 2016

(54) CYCLIZATION METHODS

(71) Applicant: REGENTS OF THE UNIVERSITY OF MINNESOTA, St. Paul, MN (US)

(72) Inventors: Thomas R. Hoye, St. Paul, MN (US); Beeraiah Baire, St. Paul, MN (US); Dawen Niu, St. Paul, MN (US); Patrick H. Willoughby, St. Paul, MN (US); Brian P. Woods, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 486 days.

(21) Appl. No.: 13/756,069

(22) Filed: Jan. 31, 2013

(65) Prior Publication Data

US 2013/0197241 A1    Aug. 1, 2013

Related U.S. Application Data

(60) Provisional application No. 61/593,127, filed on Jan. 31, 2012.

(51) Int. Cl.
| | | |
|---|---|---|
| *C07D 307/93* | (2006.01) | |
| *C07D 307/88* | (2006.01) | |
| *C07D 491/048* | (2006.01) | |
| *C07D 493/04* | (2006.01) | |
| *C07D 493/14* | (2006.01) | |
| *C07F 7/08* | (2006.01) | |
| *C07F 7/18* | (2006.01) | |
| *C07D 311/94* | (2006.01) | |

(52) U.S. Cl.
CPC ............ *C07F 7/083* (2013.01); *C07D 307/88* (2013.01); *C07D 311/94* (2013.01); *C07D 491/048* (2013.01); *C07D 493/04* (2013.01); *C07D 493/14* (2013.01); *C07F 7/0827* (2013.01); *C07F 7/1876* (2013.01); *C07F 7/1892* (2013.01)

(58) Field of Classification Search
None
See application file for complete search history.

(56) References Cited

PUBLICATIONS

Bharucha, et al., J. Am. Chem. Soc., 114:3120 (1992).*
Hoye, "The Hexadehydro-Diels-Alder Reaction and Other Musings," Roush 60th Birthday Celebration Symposium, Scripps-Florida, Jupiter, FL, 132 pages (May 5, 2012).
Hoye et al., "The Hexadehydro-Diels-Alder Reaction," Paquette Legacy Symposium, The Ohio State University, Columbus, OH, 130 pages (May 19, 2012).
Hoye et al., "The Hexadehydro-Diels-Alder (HDDA) Reaction," Departmental Seminar, Department of Chemistry, University of Minnesota, Minneapolis, MN, 124 pages (Sep. 6, 2012).
Hoye et al., "The Hexadehydro-Diels-Alder (HDDA) Reaction," University of Houston, Houston, TX, 125 pages (Nov. 27, 2012).
Hoye et al., "The Hexadehydro-Diels-Alder (HDDA) Reaction," Department of Chemistry, University of St. Thomas, St. Paul, MN, 137 pages (Dec. 14, 2012).
Hoye et al., "The Hexadehydro-Diels-Alder (HDDA) Reaction," Department of Chemistry, University of Nevada, Reno; Reno, NV, 149 pages (Jan. 18, 2013).
Hoye et al., "The Hexadehydro-Diels-Alder (HDDA) Reaction," Department of Chemistry, University of Oregon, Corvallis, OR, 162 pages (Jan. 24, 2013).
Hoye et al., "The Hexadehydro-Diels-Alder (HDDA) Reaction," Department of Chemistry, Portland State University, Portland, OR, 169 pages (Jan. 25, 2013).
Hoye et al., "A Nanoparticle-Based Drug Delivery Strategy Enabled by Flash Nanoprecipitation (FNP) of Novel Silicate Ester Prodrugs and PEG-PLGA," Applied Chemistry Lecture, Changchun Institute of Applied Chemistry, Changchun, PRC, 65 pages (Aug. 17, 2012).
Hoye et al., "A Nanoparticle-Based Drug Delivery Strategy Enabled by Flash Nanoprecipitation (FNP) of Novel Silicate Ester Prodrugs and PEG-PLGA," 1$^{st}$ International Symposium on Polymer Ecomaterials, Changchun, Jilin Province, PRC, 52 pages (Aug. 22, 2012).
Hoye et al., "From Spontaneous (Biosynthetic Events) to Serendipitous (Benzyne) Reactions," University of Puerto Rico, Rio Piedras, San Juan, PR (Spontaneous to Serendipitous), 163 pages (Mar. 21, 2012).
Hoye et al., "From Spontaneous (Biosynthetic Events) to Serendipitous (Benzyne) Reactions," Michigan State University, Lansing, MI, 167 pages (Apr. 19, 2012).
Hoye et al., "From Spontaneous (Biosynthetic Events) to Serendipitous (Benzyne) Reactions," Chem 2920, Topics in Chemistry, University of Minnesota, Minneapolis, MN, 101 pages (Apr. 26, 2012).
Hoye et al., "From Spontaneous (Biosynthetic Events) to Serendipitous (Benzyne) Reactions: The Hexadehydro-Diels-Alder (HDDA) Reaction," Sogang University, Seoul, Korea, 142 pages (Aug. 13, 2012).
Hoye et al., "From Spontaneous (Biosynthetic Events) to Serendipitous (Benzyne) Reactions: The Hexadehydro-Diels-Alder (HDDA) Reaction," Yonsei University, Seoul, Korea, 142 pages (Aug. 14, 2012).
Hoye et al., "From Spontaneous (Biosynthetic Events) to Serendipitous (Benzyne) Reactions: The Hexadehydro-Diels-Alder (HDDA) Reaction," Seoul National University, Seoul, Korea, 145 pages (Aug. 16, 2012).
Hoye et al., "From Spontaneous (Biosynthetic Events) to Serendipitous (Benzyne) Reactions: The Hexadehydro-Diels-Alder (HDDA) Reaction," Northeast Normal University, Changchun, Jilin Province, PRC, 156 pages (Aug. 21, 2012).
Wang et al., "Metal-catalyzed formation of fluorinated arenes from jult-ynes", Abstract 355, ACS Meeting (Aug. 2012).

(Continued)

*Primary Examiner* — Michael Barker
(74) *Attorney, Agent, or Firm* — Viksnins Harris & Paddys PLLP

(57) ABSTRACT

The invention provides methods for cyclizing poly-yne compounds under mild conditions to provide cyclic compounds.

6 Claims, No Drawings

(56) References Cited

PUBLICATIONS

Baire et al., "Synthesis of complex benzenoids via the intermediate generation of o-benzynes through the hexadehydro-Diels-Alder reaction", Nature Protocols 8 (3), 501-508. (doi:10.1038/nprot.2013.017) (2013).
Bradley et al., "Thermolysis of 1,3,8-Nonatriyne: Evidence for Intramolecular [2+4] Cycloaromatization to a Benzyne Intermediate", J. Am. Chem. Soc., 119, 9917-9918 (1997).
Cahill et al., "New Thermal Routes to ortho-Benzyne", Aust. J. Chem., 63, 1007-1012 (2010).
Chen et al., "Cycloaddition Reactions of Azide, Furan, and Pyrrole Units with Benzynes Generated by the Hexadehydro-Diels-Alder (HDDA) Reaction," Heterocycles 88 (2), 1191-1200 (2014).
Hoye et al., "The hexadehydro-Diels-Alder reaction," Nature 490 (7419), 208-212 (doi:10.1038/nature11518)(2012).
Hoye, "Tactics for probing aryne reactivity: mechanistic studies of silicon—oxygen bond cleavage during the trapping of (HDDA-generated) benzynes by silyl ethers", Chem. Sci. 5, 545-550 (2014).
Johnson, "Dehydropericyclic routes to reactive intermediates", J. Phys. Org. Chem., 23, 283-292 (2010).
Kawano et al., "Synthesis of indenothiophenone derivatives by clycloaromatization of non-conjugated thienyl tetraynes", Tetrahedron Letters, 46, 1233-1236 (2005).
Kawano et al., "Effect of Water Molecules on the Cycloaromatization of Non-Conjugated Aromatic Tetraynes", Bull. Chem. Soc., vol. 79 (6), 944-949 (2006).
Kitamura, "Synthetic Methods for the Generation and Preparative Application of Benzyne", Aust. J. Chem., 63, 987-1001 (2010).
Lee et al., "Silver-mediated fluorination, trifluoromethylation, and trifluoromethylthiolation of arynes", Chem. Sci, 4, 3205-3211 (2013).
Lee et al., "Alder-Ene Reactions of Arynes", Org. Lett. 15 (8), 1938-1941 (2013).
Lee et al., "Regioselectivity in the Nucleophile Trapping of Arynes: The Electronic and Steric Effects of Nucleophiles and Substituents", Org. Lett. 16, 6-9 (2014).
Miyawaki et al., "Multiple Cycloaromatization Bearing a Triggering Device on the Terminal Acetylene of Novel Aromatic Enediynes Carbon", Tetrahedron Letters 39, 6923-6926 (1998).
Niu et al., "The aromatic ene reaction," Nature Chem. advance online publication, Nov. 17, 2013. (doi:10.1038/nchem.1797).
Niu et al., "Alkane desaturation by concerted double hydrogen atom transfer to benzyne", Nature 2013, 501, 531-534. (2013) (doi:10.1038/nature12492).
Sterenberg et al., "A Metal-Templated 4 + 2 Cycloaddition Reaction of an Alkyne and a Diyne to Form a 1,2-Aryne", Organometallics, 28, 4906-4908 (2009).
Torikai et al., "Synthesis and DNA cleaving activity of water-soluble non-conjugated thienyl tetraynes", Bioorganic & Medicinal Chemistry, 16, 5441-5451 (2008).
Ueda et al., "Cycloaromatization of a Non-Conjugated Polyenyne System: Synthesis of 5H-Benzo [d] fluoreno[3,2-b]pyrans via Diradicals Generated from 1-2[2- {4-(2-Alkoxymethylphenyl)butan-1,3-diynyl}]phenylpentan-2,4-diyn-1-ols and Trapping Evidence for the 1,2-Didehydrobenzene Diradical", Tetrahedron Letters, vol. 38 (22), 3943-3946 (1997).
Ueda et al., "An Unprecedented Arylcarbene Formation in Thermal Reaction of Non-Conjugated Aromatic Enetetraynes and DNA Strand Cleavage", Tetrahedron Letters 40, 319-322 (1999).
Ueda et al. "Domino thermal radical cycloaromatization of non-conjugated aromatic hex- and heptaynes: synthesis of fluoranthene and benzo[a]rubicene skeletons", Tetrahedron Letters 41, 1447-1451 (2000).
Ueda et al., "Synthesis of Indeno[1,2-b]Phenanthrene-Type Heterocycles by Heterocycles Cycloaromatization of Acyclic Non-Conjugated Benzotetraynes", Heterocycles, vol. 54 (2), 887-900 (2000).
Yun et al., "Alkane C-H Insertion by Aryne Intermediates with a Sliver Catalyst", J. Am. Chem. Soc. 135, 4668-4671 (2013).

* cited by examiner

CYCLIZATION METHODS

RELATED APPLICATION

This application claims the benefit of U.S. Provisional Application Ser. No. 61/593,127 filed on Jan. 31, 2012, which application is herein incorporated by reference.

STATEMENT OF GOVERNMENT RIGHTS

This invention was made with government support under and R01-CA76497 and R01-GM65597 awarded by the National Institutes of Health. The government has certain rights in the invention.

BACKGROUND OF THE INVENTION

Cyclic compounds, including polycyclic compounds, are useful as dyes, pesticides, pharmaceuticals, and in the electronics industry, inter alia. Currently there is a need for methods that can be used to prepare cyclic compounds. In particular, there is a need for methods that can be carried out under mild conditions. Such methods may be particularly useful for preparing complicated cyclic ring systems as well as cyclic ring systems that possess sensitive functionality that may be damaged by the conditions required by many cyclization methods. There is also a need for methods that can lead to highly substituted cyclic ring systems.

o-Benzyne (or 1,2-didehydrobenzene, 1, Scheme 1) is one of the oldest, most interesting, and most well studied of all reactive intermediates in chemistry. Methods for generating benzynes involve the removal of two adjacent atoms or substituents from precursors 2. The multifaceted and often highly efficient reactions of benzynes with suitable trapping reagents (cf. 1 to 3) have long been exploited, often in the service of synthetic organic chemistry. Even by 1967 myriad such reactions, recorded in a substantial monograph, were known (see Hoffmann, R. W. Organic Chemistry, A Series of Monographs—Volume 11, Academic Press, New York, 1967). Nonetheless, newly discovered benzyne reaction motifs continue to emerge; this Renaissance attests to yet additional versatility of this remarkable intermediate. Nearly all benzyne trapping reactions (regardless of whether occurring via a stepwise or an asynchronous/polarized concerted mechanistic pathway) are initiated by in-plane nucleophilic attack by electron density in the trapping agent (Nu-El) on the highly strained alkyne in 1.

Scheme 1. Generic benzyne forming (2 to 1) and trapping (1 to 3) reactions.

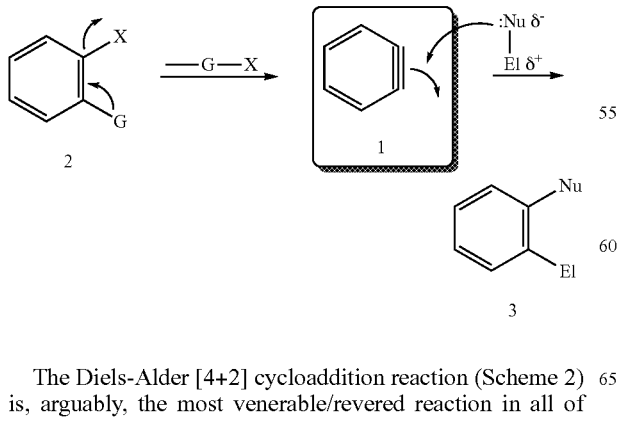

The Diels-Alder [4+2] cycloaddition reaction (Scheme 2) is, arguably, the most venerable/revered reaction in all of chemistry. The prototypical event involves addition of a 1,3-diene 4π-component (5) with an alkenyl dienophile 4 and results in a cyclohexene product 6 at the oxidation state of a tetrahydrobenzene. If an alkyne is used as the dienophile (7), a 1,4-cyclohexadiene (or 1,4-dihydrobenzene, 8 results); this can be viewed as a didehydro-Diels-Alder reaction. Another well-known variant involves engagement of a (yet more highly oxidized) 1,3-enyne (9) as the 4π-component with an alkyne (7). This produces a transient cyclic allene 10 that rapidly rearranges via a [1,5]-hydrogen atom shift to produce (the yet more highly oxidized) benzene (11).

Scheme 2.

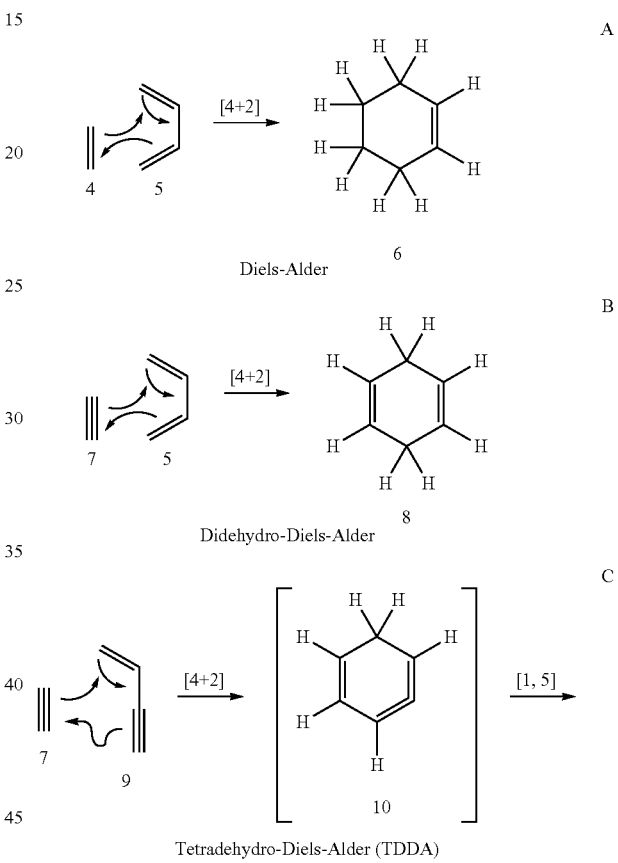

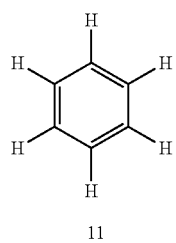

-continued

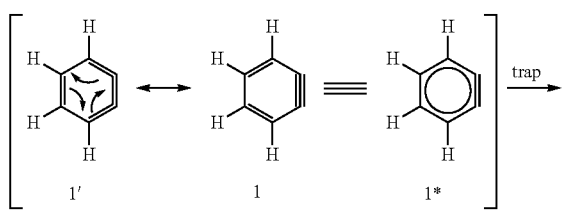

Hexadehydro-Diels-Alder (HDDA)
Protypes of the A. classic Diels-Alder, B. Didehydro-Diels-Alder, C. Tetradehydro-Diels-Alder (TDDA), and D. Hexadehydro-Diels-Alder (HDDA, this work) reactions.

The most highly oxidized Diels-Alder variant is the cycloaddition between a 1,3-diyne 12 and an alkynyl diynophile (7), which generates o-benzyne directly. Given the potential generality of this reaction, it is surprising that it has not been highly exploited. However, 4+2 cyclizations leading to benzynes have received only limited attention. See for example, K. Miyawaki, et al., *Tetrahedron Lett.*, 1997, 38, 3943-3946; A. Bradley and R. Johnson, *J. Am. Chem. Soc.*, 1997, 119, 9917-9918; K. Miyawaki, et al., *Tetrahedron Lett.*, 1998, 39, 6923-6926; I. Ueda, et al., *Tetrahedron Lett.*, 1999, 40, 319-322; I. Ueda, et al., *Tetrahedron Lett.*, 2000, 41, 1447-1451; K. Miyawaki, et al., *Heterocycles.*, 2000, 54, 887-900; T. Kawano, et al., *Tetrahedron Lett.*, 2005, 46, 1233-1236; T. Kawano, et al., *Bull. Chem. Soc, Jpn.*, 2006, 79, 944-949; K. Torikai, et al., *Bioorganic and Medicinal Chemistry*, 2008, 16, 5441-5451; J. Tsui and B. Sterenberg, *Organometallics*, 2009, 28, 4906-4908; R. Johnson, *J. Phys. Org. Chem.*, 2010, 23, 283-292; T. Kitamura, *Aust. J. Chem.*, 2010, 63, 987-1001; and K. Cahill, et al., *Aust. J. Chem.*, 2010, 63, 1007-1012.

SUMMARY OF THE INVENTION

Applicant has discovered a mild method that allows for the preparation of polycyclic ring systems by the cyclization of poly-yne compounds. Accordingly, in one embodiment the invention provides a method comprising, cyclizing a tri-yne compound at a temperature below about 300° C. to provide a polycyclic compound.

In one embodiment the invention provides a method comprising, cyclizing a nonaromatic compound comprising at least three alkyne groups at a temperature below about 300° C. to provide a polycyclic compound.

In one embodiment the invention provides a method comprising cyclizing a poly-yne compound of formula I:

$$W-X-Y \quad (I)$$

at a temperature below about 300° C. to provide a polycyclic compound, wherein:

W is an organic group that comprises two or more alkyne groups;

X is selected from a) a linking group that comprises 2-20 carbon atoms and at least one severable group, or b) a non-aromatic linking group that comprises 2-20 carbon atoms; and Y is an organic group that comprises at least one alkyne group.

Applicant has also discovered a mild method that allows for the preparation of cyclic systems by the intermolecular cyclization of a first compound that comprises two or more alkyne groups with a second compound that comprises at least one alkyne group. Accordingly, in one embodiment the invention provides a method comprising, cyclizing a first compound that comprises two or more alkyne groups with a second compound that comprises at least one alkyne group at a temperature below about 300° C. to provide a corresponding cyclic compound. Applicant has also discovered a mild method that allows for the preparation of cyclic systems by associating a first compound that comprises two or more alkyne groups and a second compound that comprises at least one alkyne group with a template such that the first compound and the second compound are properly aligned to allow for the formation of a cyclic compound from the intermolecular cyclization of at least three alkyne groups from the first compound and the second compound. Accordingly, in one embodiment the invention provides a method comprising, associating a first compound that comprises two or more alkyne groups and a second compound that comprises at least one alkyne group with a template such that the first compound and the second compound are properly aligned to allow for the formation of a cyclic compound from the intermolecular cyclization of at least three alkyne groups from the first compound and the second compound.

In one embodiment the invention provides a method comprising, 1) associating a first compound that comprises two or more alkyne groups and a second compound that comprises at least one alkyne group with a template such that the first compound and the second compound are properly aligned to allow for the formation of a cyclic compound from the intermolecular cyclization of at least three alkyne groups from the first compound and the second compound, and 2) allowing at least two alkyne groups from the first compound and one alkyne of the second compound to cyclize to form a first cyclic compound.

The invention also provides compounds and materials prepared according to the methods of the invention.

DETAILED DESCRIPTION

In the course of an otherwise unrelated study, an attempt was made to prepare the ketotetrayne 14 by oxidation of the precursor alcohol 13 with manganese dioxide (Scheme 3). Surprisingly, the major product from this experiment, formed in about 6 hours, was the (hexasubstituted) benzene derivative 15 (53% yield after purification). From this result it was postulated that the benzyne intermediate 16/16' was being both readily formed and efficiently trapped by the oxygen atom in the fortuitously placed siloxyethyl group. Migration of the silyl group from O to C within zwitterion 17 would account for formation of 15.

Scheme 3. Applicant's first example of Hexadehydro-Diels-Alder reaction (HDDA).

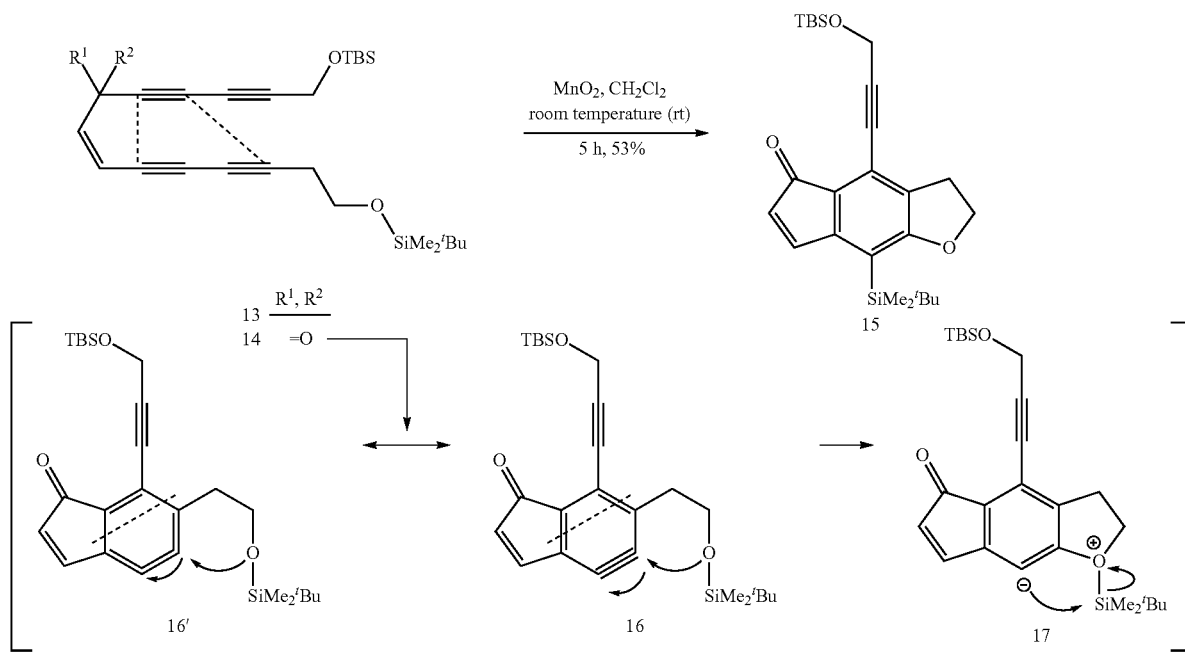

Another specific example is the cyclization of tri-yne 21 to tetracycle 22 at ambient temperature and with high yield. The synthesis of substrate 21 is shown in Scheme 4. It is representative of the routes that are used to prepare many of the substrates shown as examples of the invention elsewhere in this document. In particular, a Sonogashira cross-coupling of 18 with 19 gives the enediyne 20. Addition of an alkynyl anion (here, trimethylsilylethynyllithium) and oxidation of the resulting propargylic alcohol gives the triynone 21. Cyclization of 21 occurs in chlorinated hydrocarbon solvents (dichloromethane, chloroform, 1,2-dichloroethane, 1,2-dichlorobenzene), acyclic hydrocarbon solvents (heptane, hexane, hexanes, petroleum ether), and aromatic solvents (e.g., toluene or benzene).

Scheme 4. One specific example of substrate synthesis (18 to 21) and its cyclization to polycyclic product 22 under mild conditions.

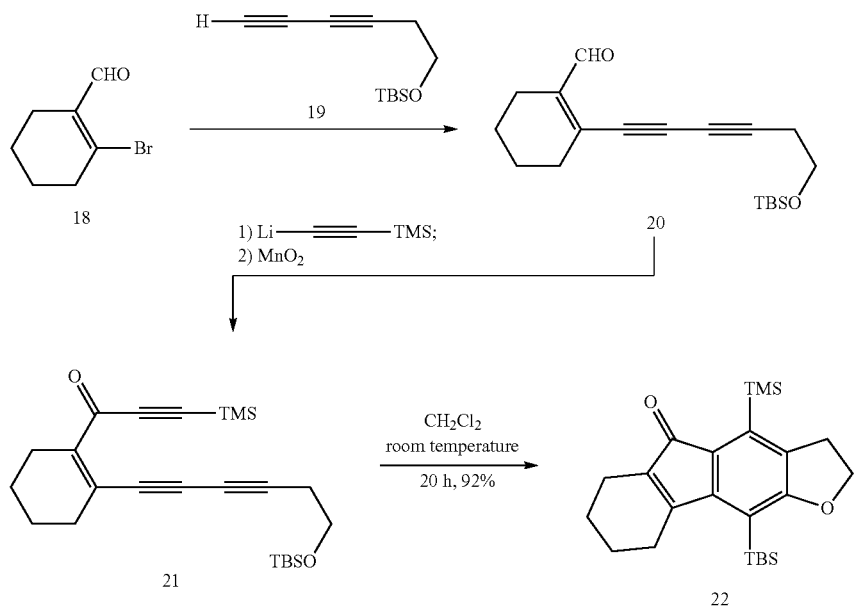

Subsequent studies that are described herein have shown i) the efficiency and generality of this cyclization reaction; ii) the easy accessibility of poly-yne substrates via convergent assembly strategies; and iii) an enticingly wide variety of trapping reactions, including some that are unique to the reagent-free conditions used for these thermal cycloisomerizations. Each of the benzyne-generating and -trapping stages considerably increases product structural complexity, thereby amplifying the overall impact of these tandem transformations. Thus, the cyclization methods of the invention are generally useful for preparing a wide array of cyclic compounds that are useful as dyes, pesticides, pharmaceuticals, and in the electronics industry, inter alia. The methods of the invention can be carried out under mild conditions. Accordingly, they may be particularly useful for preparing complicated cyclic ring systems as well as cyclic ring systems that possess sensitive functionality.

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, hexyl, or iso-hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term saccharide includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995. A saccharide can conveniently be linked to the remainder of a compound through an ether bond.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

As used herein the term tri-yne includes compounds that have only three alkyne groups. The tri-yne can include any other organic functionalities, provided they do not interfere with the cyclization reactions.

The term "nonaromatic compound" means a poly-yne compound that does not include an aromatic group (e.g. an aryl or heteroaryl) in the portion of the compound between the di-yne and the alkyne that cyclize with one another, according to the methods of the invention. The nonaromatic compound includes "aromatic-free compounds," which are poly-ynes that do not comprise any aromatic groups whatsoever.

The term "cyclic" includes both monocyclic and polycyclic systems. In one embodiment of the invention the term cyclic is a monocyclic ring system or compound. In another embodiment of the invention the term cyclic is a polycyclic ring system or compound.

In one embodiment W comprises 2, 3, 4, or 5 alkyne groups.

In one embodiment W comprises 2, or 3 alkyne groups.

In one embodiment X is a linking group that comprises 2-20 carbon atoms and at least one severable group.

In one embodiment X is a linking group that comprises 2-10 carbon atoms and at least one severable group.

In one embodiment the severable group is selected from an ester, an amide, a carbonate, a carbamate, an ether, a silylether, an alkene, a urea, a sulfide, a disulfide, a borate ester, a borinate ester, an aluminate ester, a silicate ester, a hydrazine, an azo moiety, a sulfone, a phosphate ester, and a phosphonate ester.

In one embodiment X is a non-aromatic linking group that comprises 2-20 carbon atoms. It is to be understood that the linking group, in addition to comprising 2-20 carbon atoms, can also optionally comprise one or more heteroatoms (e.g. O, S, N, or P) or one or more carbonyl groups.

In one embodiment X is a non-aromatic linking group that comprises 2-10 carbon atoms. It is to be understood that the linking group, in addition to comprising 2-10 carbon atoms, can also optionally comprise one or more heteroatoms (e.g. O, S, N, or P) or one or more carbonyl groups.

In one embodiment of the invention X is a divalent, branched or unbranched, saturated or unsaturated, hydrocarbon chain, having from 1 to 20 carbon atoms, which chain can optionally be substituted on carbon with one or more substituents selected from the group consisting of $(C_1-C_6)$ alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, amino acid, peptide, saccharide, and heteroaryloxy; wherein one or more of the carbon atoms in the chain can optionally be replaced with —O—, -aryl-, heteroaryl, or —N(R)—; each R is independently H or $(C_1-C_6)$alkyl; and wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, cyano, nitro, halo, or hydroxy.

In one embodiment of the invention X is a divalent, branched or unbranched, saturated or unsaturated, hydrocarbon chain, having from 1 to 20 carbon atoms, wherein one or more of the carbon atoms is optionally replaced by (—O—) or (—NR—), and wherein the chain is optionally substituted on carbon with one or more oxo substituents.

In one embodiment of the invention X is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$ alkoxycarbonyl, $(C_1-C_6)$alkylthio, azido, cyano, nitro, halo, hydroxy, oxo, carboxy, aryl, aryloxy, heteroaryl, amino acid, peptide, saccharide, and heteroaryloxy.

In one embodiment of the invention X is a divalent, branched or unbranched, saturated or unsaturated, hydrocarbon chain, having from 3 to 15 carbon atoms, wherein one or more of the carbon atoms is optionally replaced by (—O—) or (—NR—), and wherein the chain is optionally substituted on carbon with one or more oxo substituents.

In one embodiment of the invention X is a divalent, branched or unbranched, saturated or unsaturated, hydrocarbon chain, having from 3 to 15 carbon atoms, wherein the chain is optionally substituted on carbon with one or more oxo substituents.

In one embodiment of the invention X is a divalent, branched or unbranched, hydrocarbon chain, having from 4 to 8 carbon atoms, wherein the chain is optionally substituted on carbon with one or more oxo substituents.

In one embodiment of the invention X is a peptide.
In one embodiment of the invention X is an amino acid.

In one embodiment of the invention X is a saccharide. In one embodiment of the invention X is a monosaccharide. In one embodiment of the invention X is a disaccharide.

In one embodiment of the invention X comprises a monocyclic or bicyclic aryl or heteroaryl ring.

In one embodiment of the invention X comprises a monocyclic aryl or monocyclic heteroaryl ring.

In one embodiment of the invention X is a comprises a phenyl ring.

In one embodiment of the invention X is:

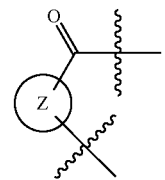

wherein Z is a monocyclic or bicyclic aryl or bicyclic heteroaryl ring. In one embodiment of the invention Z is a monocyclic aryl or monocyclic heteroaryl ring.

In one embodiment of the invention X is:

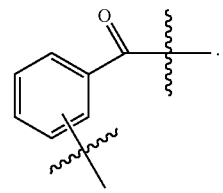

In one embodiment of the invention X is:

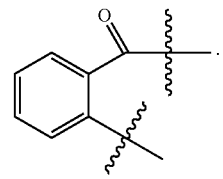 [SMILES: *C(=O)c1ccccc1*]

In one embodiment Y comprises 1, 2, 3, or 4 alkyne groups.

In one embodiment Y comprises 1 or 2 alkyne groups.

In one embodiment Y has only 1 or 2 alkyne groups.

Benzyne Trapping Reagents

The methods of the invention can also further comprise trapping the benzyne intermediates formed by cyclization with a suitable benzyne trapping reagent. This trapping can be used to terminate the cyclization reaction and form the final product, for example, by adding hydrogen to the benzyne intermediate, or this trapping can be used to further elaborate the benzyne intermediate to provide a final product, for example, by incorporating all or a portion of a trapping molecule into the final product. A number of benzyne trapping reagents are known in the field of organic chemistry; for example, see T. Kitamura, *Aust. J. Chem.*, 2010, 63, 987-1001. Hoffmann, R. W. Organic Chemistry, A Series of Monographs—Volume 11, Academic Press, New York, 1967.

In one embodiment of the invention, the benzyne trapping reagent is an aromatic agent like phenol, furan, 2H-pyrone, benzene, naphthalene, anthracene, phenanthrene, tetracene, pentacene, 6-membered heteroaromatic compounds containing one to four nitrogen atoms (pyridine, pyridazine, pyrazine, pyrimidine, triazines, tetrazines), fused bicyclic heteroaromatic compounds containing 1-4 nitrogen atoms (quinoline, isoquinoline, quinazoline, quinoxaline, cinnoline, indole, isoindole, benzofuran, isobenzofuran) and their substituted derivatives.

In one embodiment of the invention, the benzyne trapping reagent is a formal hydrogen molecule ($H_2$) donor like a cyclic hydrocarbon (e.g., cyclopentane, indane, taxadiene, cyclooctane, or cycloheptane), a cyclic ether (e.g., tetrahydrofuran or p-dioxane), or a cyclic amine (e.g., N-methylpiperidine, quinuclidine, or 1,4-diaza[2.2.2]bicyclooctane).

In one embodiment of the invention, the benzyne trapping reagent is an oxygen-based nucleophile of protic [phenol, alcohol, carboxylic acid, amide, carbamate, hydrogen peroxide, alkyl hydroperoxide, peroxyacid (or their anionic conjugate bases)] or aprotic [ether, dialkyl peroxide, acyl alkyl peroxide, diacylperoxide] nature.

In one embodiment of the invention, the benzyne trapping reagent is a sulfur containing nucleophile like a thiol, sulfide, thioester, thioacid, sulfenic acid, sulfinic acid (or their anionic conjugate bases) sulfenic ester, or sulfinic ester; a sulfur containing nucleophile like a thiol, sulfide, thioester, thioacid, sulfenic acid, sulfinic acid (or their anionic conjugate bases) sulfenic ester, sulfinic ester, disulfides, thiosulfonates.

In one embodiment of the invention, the benzyne trapping reagent is a selenium-containing reagent like a selenol, selenide, or diselenide.

In one embodiment of the invention, the benzyne trapping reagent is a phosphorous-containing nucleophile like a phosphine, a phosphite, a phosphoramide, a phosphoramidate, or a phosphinamide.

In one embodiment of the invention, the benzyne trapping reagent is a nitrogen-containing nucleophile like ammonia, a primary amine, a secondary amine, a tertiary amine, an amide, a carbamate, an imide, an imine, a hydrazine, a hydrazide, a hydrazone, an azo compound, an isonitrile, a nitrile, or cyanide ion.

In one embodiment of the invention, the benzyne trapping reagent is a halogen source like an ammonium salt of a fluoride, chloride, bromide, or iodide ion.

In one embodiment of the invention, the benzyne trapping reagent is a metal halide salt like LiX, NaX, KX, $ZnX_2$, $MgX_2$, $KBF_4$, $BX_3$, $AlX_3$, $CeX_3$, $GaX_3$, $InX_3$, $SiX_4$, $SmX_3$, $SnX_4$, $SnX_2$, $XeF_2$, CuX, $CuX_2$, $NiX_2$, $FeX_2$, $PdX_2$, $CoX_2$, $RuX_3$, $TiX_4$, $TiX_3$, or $FeX_3$.

In one embodiment of the invention, the benzyne trapping reagent is a nucleophilic initiator and ≥one molar equivalent of an electrophilic partner: e.g., the nucleophile could be a halide, alkoxide, aryloxide, thiolate, carboxylate, amine, amide, cyanide, sulfinate, and the electrophile could be an acid chloride, a carboxylic acid, a Bronsted acid, a carboxylic ester, an acylcyanide, an alkoxycarbonyl an isocyanate, a borate ester, a boronate ester, a borinate ester, an aluminate ester, a silicate ester, a haloslane, a silyltriflate, or an electrophilic halogenating agent like $X_2$, an N-halosuccinimide, Selectfluor®, a trihalide ion, 2,4,4,6-tetrahalocyclohexadienone, or polyhalogenated alkane or ketone.

In one embodiment of the invention, the benzyne trapping reagent is a hydrogen halide, a haloslane, or an alkyl halide.

In one embodiment of the invention, the benzyne trapping reagent is a pi-bond cycloaddend like carbon disulfide ($CS_2$), carbon dioxide ($CO_2$), carbonyl sulfide (CSO), an isocyanate, an isothiocyanate, a carbodiimide, a strained alkene, a strained alkyne, a vinylether, an enamine, an acrylate, an indole, an isoindole, a benzofuran, or a 1,3-dipole reagent (e.g., an alkyl or aryl azide, a nitrone, a nitrile oxide, a pyridine N-oxide, or an azomethine imine).

In one embodiment of the invention, the benzyne trapping reagent is a phenol, a furan, cyclooctane, cycloheptane, an alcohol (e.g. a $C_1$-$C_6$alcohol), or benzene.

In one embodiment of the invention, the benzyne trapping reagent is a phenol, a furan, cyclooctane, cycloheptane, or benzene.

In one embodiment of the invention, the benzyne trapping reagent is an aromatic agent, a formal hydrogen molecule ($H_2$) donor, an oxygen-based nucleophile of protic or aprotic nature, a sulfur containing nucleophile, a selenium-containing nucleophile, a phosphorous-containing nucleophile, a nitrogen-containing nucleophile, a halogen source, a metal halide salt, a hydrogen halide, an ammonium halide, a haloslane, an alkyl halide, or a pi-bond cycloaddend.

In one embodiment of the invention, the benzyne trapping reagent is an aromatic agent, a formal hydrogen molecule ($H_2$) donor, an oxygen-based nucleophile of protic or aprotic nature, a sulfur containing nucleophile, a selenium-containing nucleophile, a phosphorous-containing nucleophile, a nitrogen-containing nucleophile, a halogen source, a metal halide salt, a hydrogen halide, a haloslane, an alkyl halide, or a pi-bond cycloaddend.

Severable Groups

In one embodiment of the invention, the di-yne portion and the mono-yne of the material to be cyclized can be linked by a linking group that includes one or more severable groups. Following cyclization, these several groups can be maintained in the polycyclic product, such that the linking group forms a ring in the polycyclic product, or the severable group can be severed (e.g. hydrolyzed) to open the ring formed by the linking group. Any suitable group can be incorporated into the linking group, provided the group does not interfere with the cyclization reaction.

In one embodiment of the invention, the severable group is selected from an ester, an amide, a carbonate, a carbamate, an ether, a silylether, an alkene, a urea, a sulfide, a disulfide, a borate ester, a borinate ester, an aluminate ester, a silicate ester, a hydrazine, an azo moiety, a sulfone, a phosphate ester, and a phosphonate ester.

Templated Reactions

In one embodiment of the invention the compound that comprises two or more alkyne groups (the first compound) and the compound that comprises at least one alkyne group (the second compound) can be associated with a template that helps align the di-yne and the mono-yne groups and facilitate the intermolecular cyclization reaction.

The compounds can be associated with the template through any suitable means. For example, in one embodiment of the invention, the first compound and the second compound are associated with the template by dipole-dipole interactions or by van der Waals forces; in another embodiment of the invention, the first compound and the second compound are associated with the template by coordination; in another embodiment of the invention, the first compound and the second compound are associated with the template by hydrogen bonds; in another embodiment of the invention, the first compound and the second compound are each terminally substituted with a group that is capable of associating with the template (e.g. an amino nitrogen, a thiol, an alcohol, or a carboxylic acid).

In one embodiment the template is a metal, an inorganic molecule, an organic molecule, or a solid support. In one embodiment the template is an aluminum atom, a boron atom, a silicon atom, a titanium atom, a phosphorous atom, or a divalent metal atom (e.g. $Mg^{++}$, $Ca^{++}$, $Zn^{++}$, $Ni^{++}$, or $Fe^{++}$).

In one embodiment two alkyne groups of the first compound are aligned within about 2.8 to about 5.2 Angstroms of an alkyne group on the second compound to allow for said alkyne groups to cyclize.

Starting Materials

The starting polyalkynes used in the methods of the invention can be prepared using methods known in the field of organic chemistry, or they can be prepared using methods similar to those described in the following Schemes 5-8, wherein R, $R^1$, and $R^2$ represent any suitable organic group that will not significantly interfere with the cyclization reaction.

Scheme 5

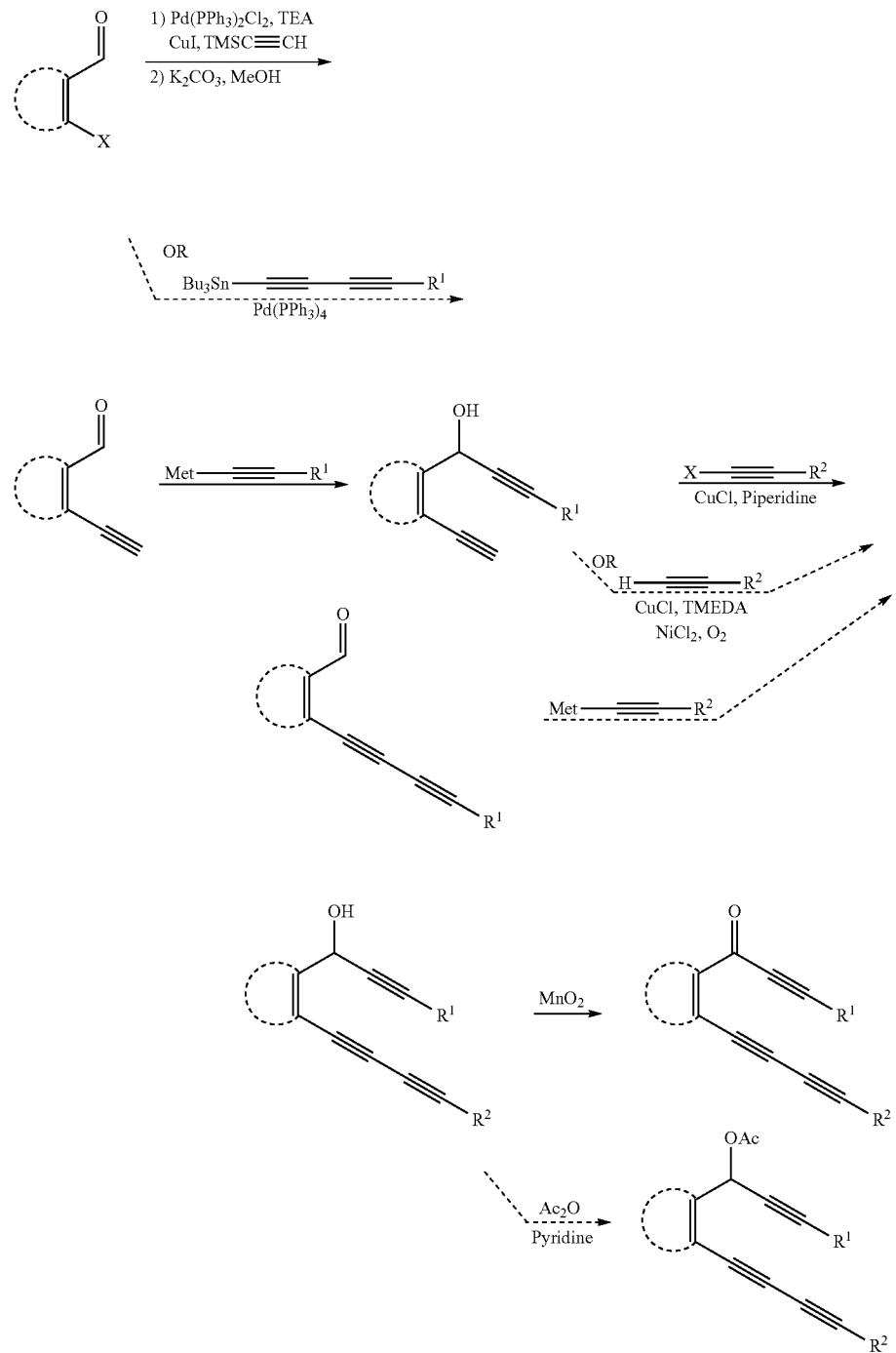

Scheme 6

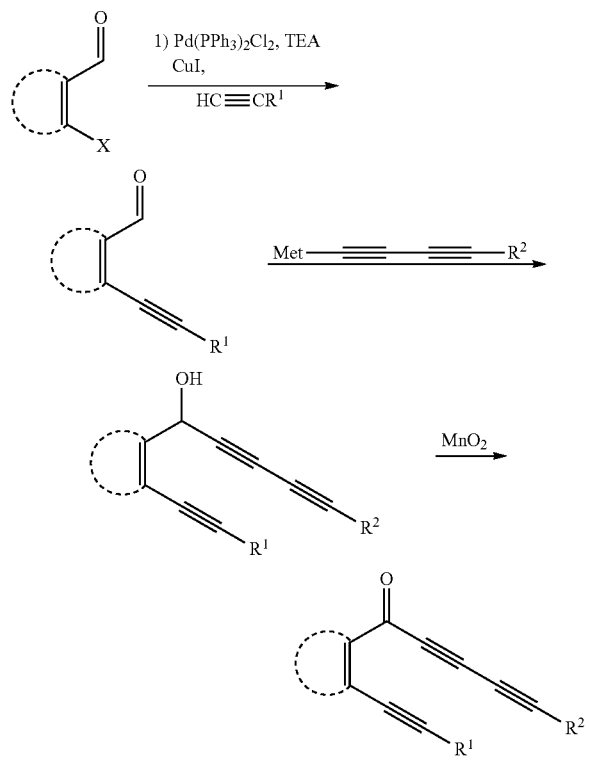

Scheme 7

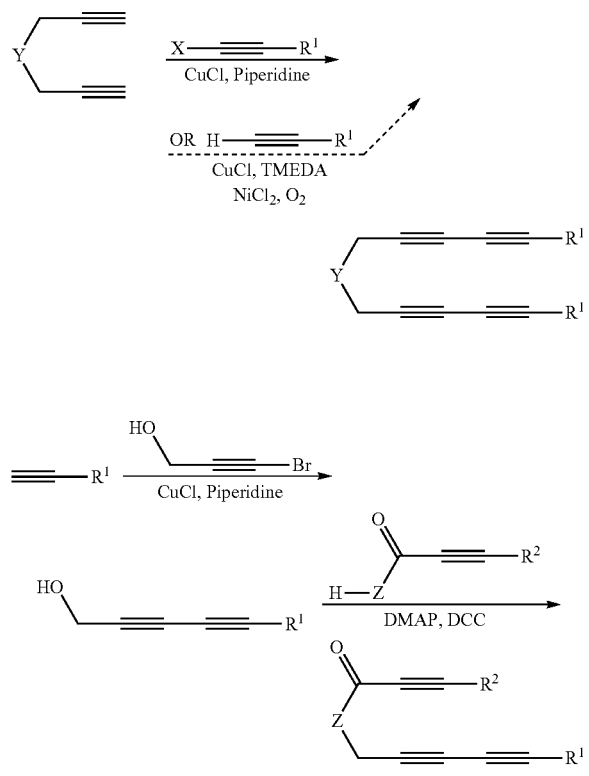

Legend of Schemes 5-8.

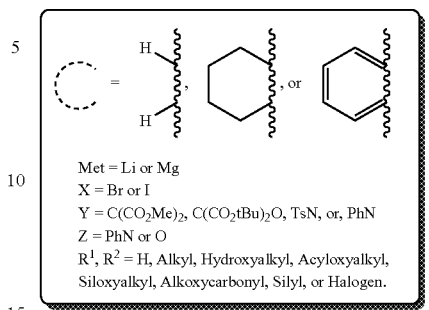

Met = Li or Mg
X = Br or I
Y = C(CO$_2$Me)$_2$, C(CO$_2$tBu)$_2$O, TsN, or, PhN
Z = PhN or O
R$^1$, R$^2$ = H, Alkyl, Hydroxyalkyl, Acyloxyalkyl, Siloxyalkyl, Alkoxycarbonyl, Silyl, or Halogen.

Schemes 5-8. Complementary, general strategies for the efficient and convergent synthesis of starting materials.

General Experimental Procedure for Each of the Key Classes of Reactions Used to Prepare the Starting Materials
General Procedure for Cadiot-Chodkiewicz Cross-Coupling of Two Alkynes.

CuCl (0.1-0.2 equiv) was added to a solution of the terminal alkyne (1 equiv) and the 1-bromoalkyne (1.1 equiv) in freshly deaerated piperidine (0.2-1.0 M) at 0° C. with stirring. After 1 hour the resulting mixture was partitioned between EtOAc and satd. aq. NH$_4$Cl. The aqueous phase was extracted with EtOAc and the combined organic extracts were washed with brine, dried over MgSO$_4$, and concentrated. Purification by MPLC or flash chromatography gave the cross-coupled conjugated diyne.

General Procedure for MnO$_2$ Oxidation

MnO$_2$ (25 equiv) was added to a solution of the ynol (1 equiv) in CH$_2$Cl$_2$ (0.3 M). This black heterogeneous mixture was vigorously stirred at room temperature. After 16 hours the reaction mixture was filtered through a plug of Celite (EtOAc eluent). Purification by either MPLC or flash chromatography gave the ynone product.

General Procedure for Glaser Coupling of Terminal Alkynes

As adapted from a procedure reported by Lei (*Org. Lett.*, 2009, 11, 709-712), CuI (0.05 equiv) and NiCl$_2$ (anhydrous, 0.05 equiv) were added to a solution of TMEDA (0.2 equiv) in THF. The resulting suspension was stirred for 2 minutes at room temperature. Terminal alkyne 1 (1 equiv) and terminal alkyne 2 (varying amounts, depending upon the preciousness) were added sequentially, and the resulting mixture was stirred under a headspace of air for 12 hours at room temperature. The resulting mixture was partitioned between EtOAc and satd. aq. NH$_4$Cl. The aqueous layer was extracted with EtOAc. The combined organic layers were washed with brine, dried with Na$_2$SO$_4$, and concentrated. The residue was purified by flash chromatography or MPLC to provide the desired cross coupled conjugated diyne.

General Procedure Alkyne Bromination:

NBS (1.1 equiv) and AgNO$_3$ (0.1 equiv) were added to a solution of terminal alkyne (1 equiv) in acetone (0.2 M) at room temperature. The flask was wrapped in aluminum foil and stirred for 2 hours. Water was added and the aqueous phase extracted 3× with EtOAc. The combined organic extracts were washed with brine, dried over MgSO$_4$, and concentrated. Purification by MPLC or flash chromatography gave the 1-bromoalkyne.

Reaction Conditions

The cyclization reactions can be carried out at any suitable temperature. Typically, the cyclization reactions are carried out at a temperature below about 300° C. In one embodiment of the invention, the cyclization reactions are carried out at a temperature below about 200° C.; in one embodiment of the invention, the cyclization reactions are carried out at a temperature below about 150° C.; in another embodiment of the invention the cyclization reactions are carried out at a temperature below about 100° C.; in another embodiment of the invention the cyclization reactions are carried out at a temperature below about 80° C.; in another embodiment of the invention the cyclization reactions are carried out at a temperature below about 50° C.; and in another embodiment of the invention the cyclization reactions are carried out at a temperature below about 30° C. In one embodiment of the invention the cyclization reactions are carried out at a temperature above about 0° C.; in another embodiment of the invention the cyclization reactions are carried out at a temperature above about 20° C.

In one embodiment, the methods of the invention are carried out in the absence of a transition metal catalyst. As used herein, the phrase "in the absence of a transition metal catalyst" means that the cyclization reaction is not catalyzed to any significant degree by a transition metal. In another embodiment, the methods of the invention are carried out in the absence of any metals (e.g. transition metals and non-transition metals).

The cyclization reactions of the invention can be carried out neat, or they can be carried out in the presence of a suitable solvent. Any suitable solvent, or combination of solvents can be used. For example, the reactions can be carried out in a suitable organic solvent. Typically, the reactions are carried out in aprotic solvents, including hydrocarbons, ethers, halocarbons, and aromatic solvents. The reactions can also be carried out in the presence of protic solvents, such as water and alcohols (e.g. methanol of tert-butanol). For example, the reactions can be carried out in hexanes, heptane, octane, chloroform (including CDCl3), dichloromethane, benzene, furan, toluene, phenol, cyclooctane, cycloheptane, cyclohexane, tetrahydrofuran, N,N-dimethylformamide, methyliodide, methanol, water, or ethyl propanoate, or mixtures thereof. In one embodiment of the invention, the solvent can include a benzyne trapping reagent, such as benzene, furan, toluene, phenol, cyclooctane, cycloheptane, or methyliodide.

Applications

The methods of the invention are useful for preparing a wide variety of cyclic compounds that may find use as dyes, pesticides, or pharmaceuticals, or in the electronics industry, inter alia. For example, the methods of the invention could be used to prepare polycyclic intermediates that could be converted to the following natural products (II-A to II-D) or pharmaceuticals (II-E and II-F), as illustrated in Schemes 9-14.

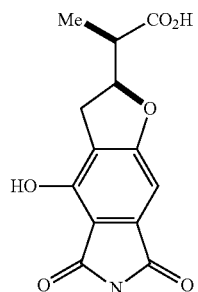

Salfredin C₁

II-A

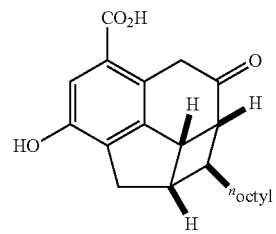

Beilschmiedic acid G

II-B

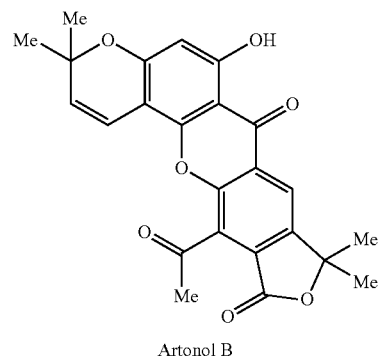

Artonol B

II-C

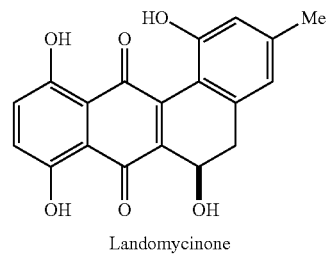

Landomycinone

II-D

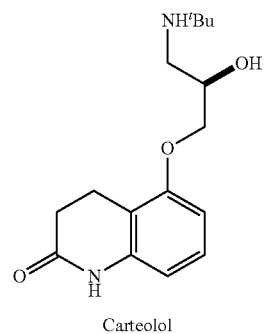

Carteolol

II-E

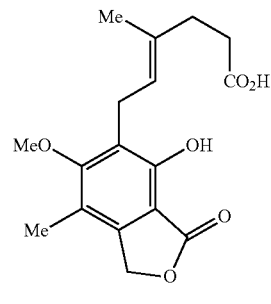

CellCept®

II-F

Salfredins $B_{11}$ (230), $A_4$ (236), and $C_1$ (II-A) (isolated from *Crucibulum* sp.) are aldose reductase inhibitors, a class of agents being developed for treatment of diabetic retinopathy and neuropathy. A cyclization reaction of the invention can be used to prepare such compounds as illustrated in Scheme 9. Cyclization of substrates 227 and 233 (via alcohol trapping within 228 and 234) will give 229 and 235. Precedented oxidations [and N-alkylation ($K_2CO_3$, $BrCH_2CO_2H$) en route to 236] will give the targets 230, 236, and II-A in 2, 4, and 3 steps, respectively.

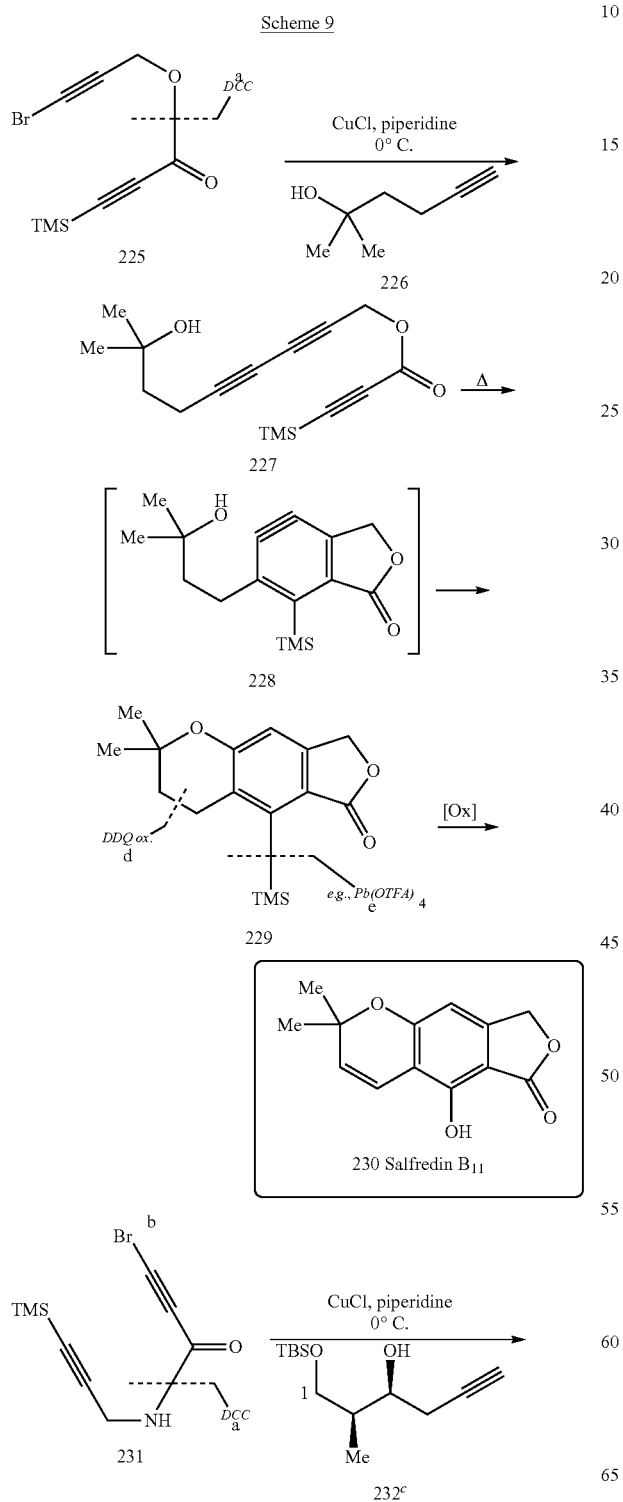

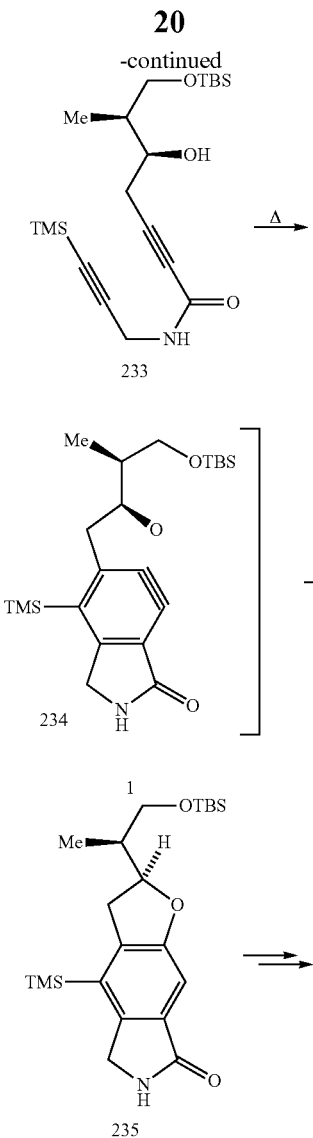

Beilschmiedic acid G (II-B) is a member of a family of antibacterial agents reported in 2011. It was isolated in Cameroon from the bark of *Beilschmiedia anacardioides*, which is known for its ancient use as a treatment for uterine cancer and infection, and is thought to be biogenetically related to the co-existing endiandric acids. A cyclization reaction of the invention can be used to prepare such a compound as illustrated in Scheme 10.

Scheme 10

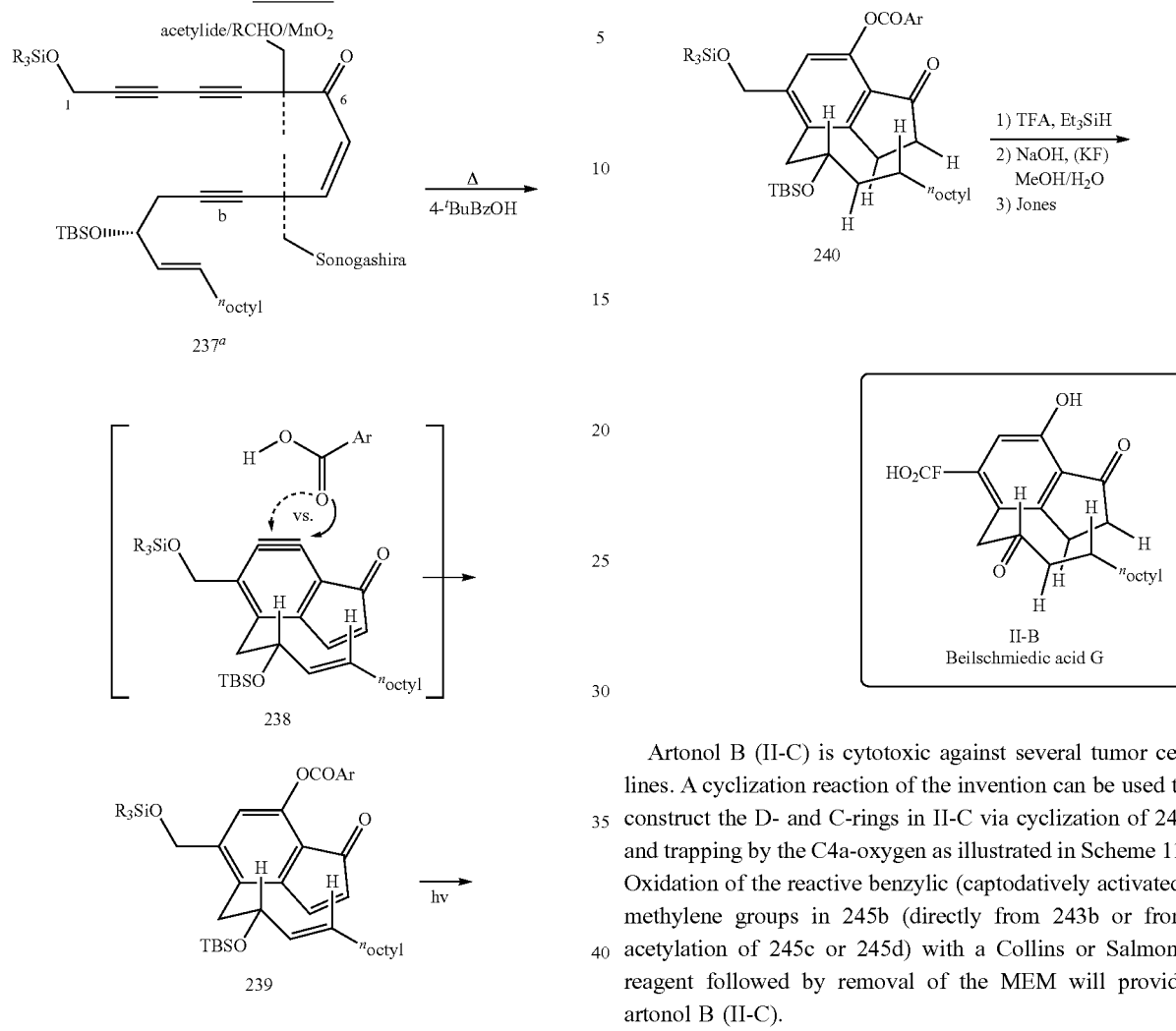

Artonol B (II-C) is cytotoxic against several tumor cell lines. A cyclization reaction of the invention can be used to construct the D- and C-rings in II-C via cyclization of 243 and trapping by the C4a-oxygen as illustrated in Scheme 11. Oxidation of the reactive benzylic (captodatively activated) methylene groups in 245b (directly from 243b or from acetylation of 245c or 245d) with a Collins or Salmond reagent followed by removal of the MEM will provide artonol B (II-C).

Scheme 11

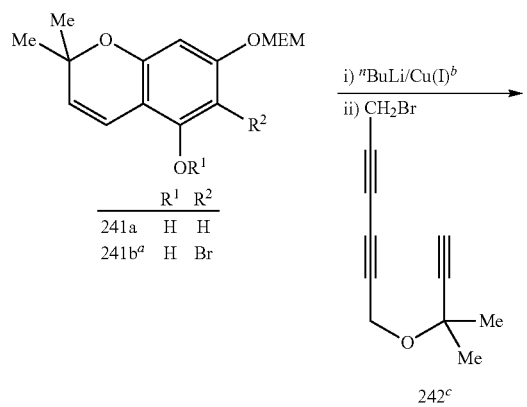

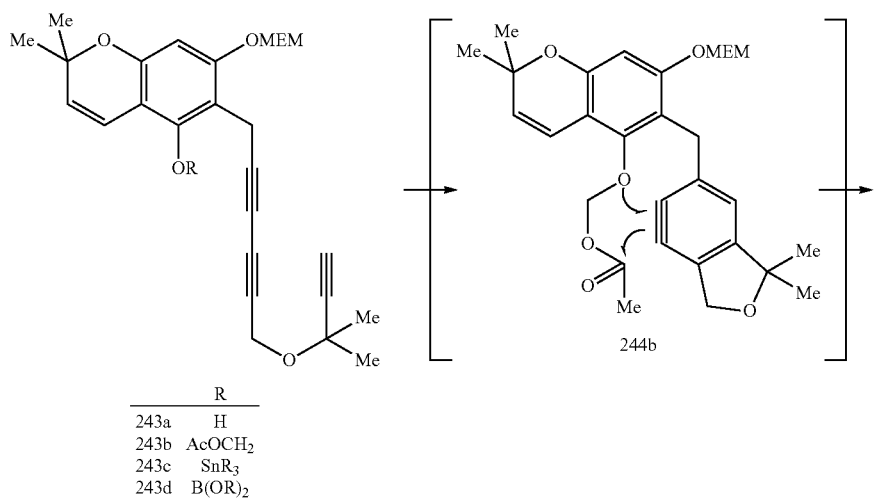

| | R |
|---|---|
| 243a | H |
| 243b | AcOCH$_2$ |
| 243c | SnR$_3$ |
| 243d | B(OR)$_2$ |

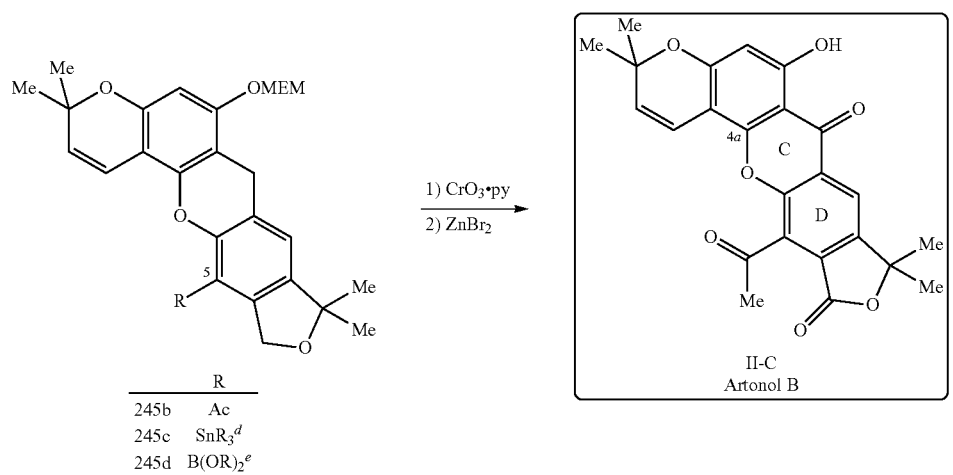

| | R |
|---|---|
| 245b | Ac |
| 245c | SnR$_3^d$ |
| 245d | B(OR)$_2^e$ |

Landomycinone (II-D) is the aglycone core of the angucyclin antibiotics. A cyclization reaction of the invention can be used to prepare such a compound as illustrated in Scheme 12. Diyne 246 can be prepared following the protocol of Vollhardt for analogous diynes from 3-hydroxyphthalide. Bromoalkyne 247b can be made from known 247a. Cross-coupling of the bis-propargylic alcohol 246 with 247 followed by diol oxidation gives the diketone 248. The key C—C-bond forming event within the highly electrophilic benzyne 249 is a silylphenol-ene addition. Synthesis of II-D can be completed by thermal retro-DA extrusion of CpH, B-ring oxidation in 250, and O-TBS cleavage. Successful reduction of this phenolic-ene strategy to practice would represent a non-trivial advance in efficiency vis-à-vis the two existing routes to II-D. It would also pave the way for use of this tactic for other related families of highly oxygenated polycyclic natural products of contemporary biological import (e.g., kibdelones and pradimicin).

Scheme 12

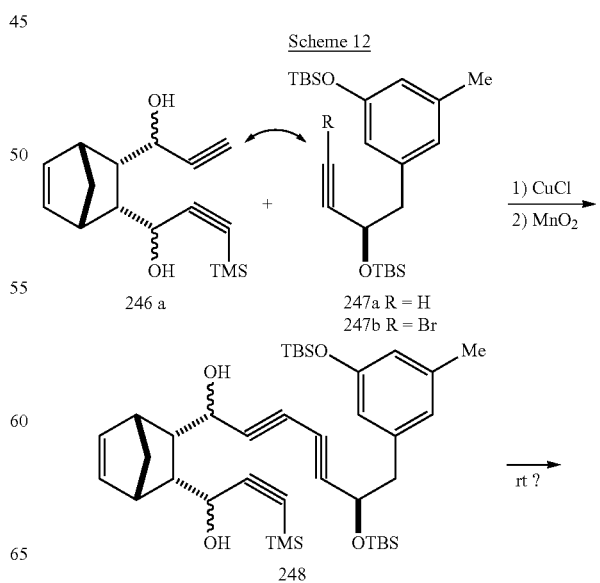

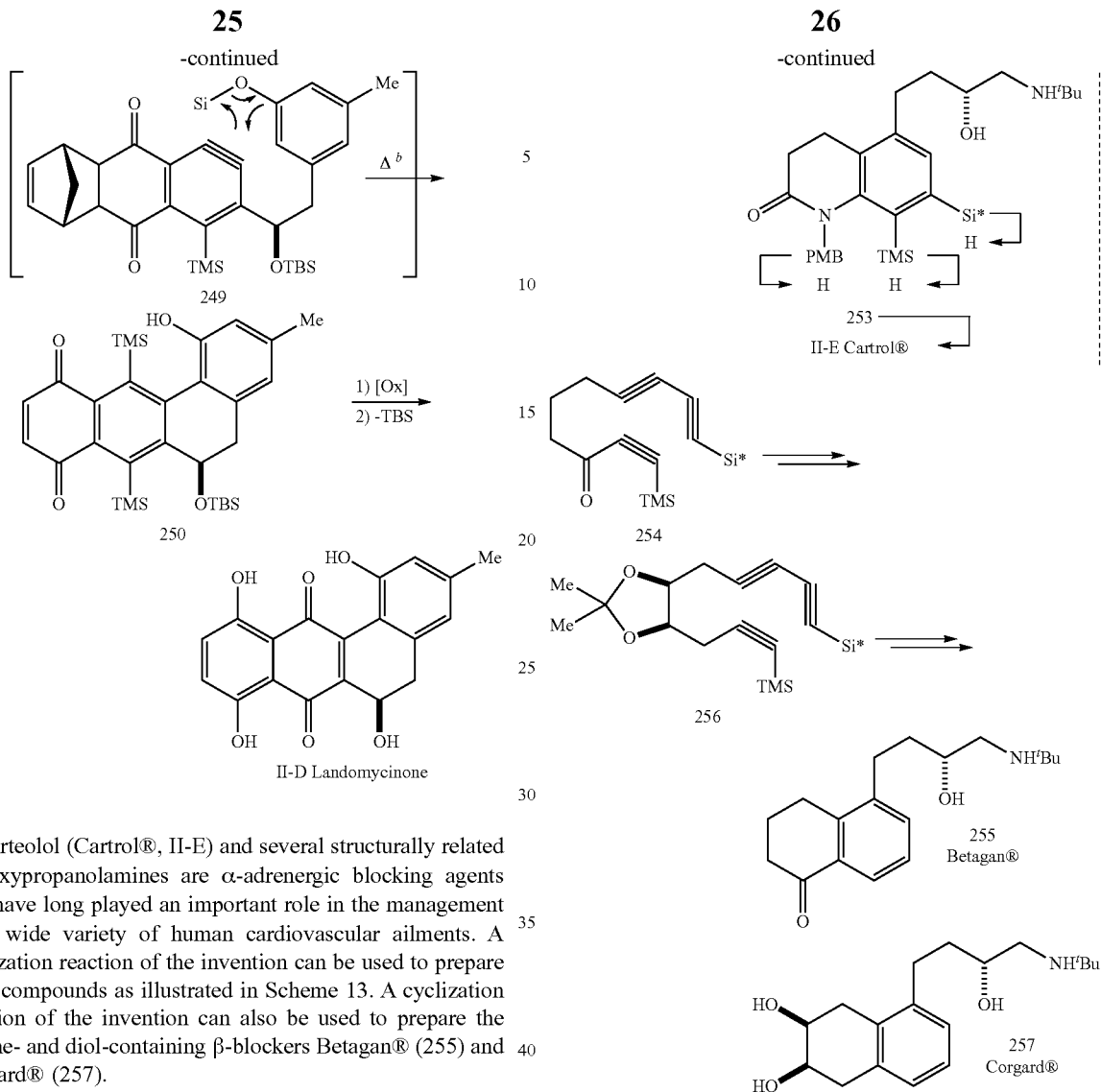

Carteolol (Cartrol®, II-E) and several structurally related aryloxypropanolamines are α-adrenergic blocking agents that have long played an important role in the management of a wide variety of human cardiovascular ailments. A cyclization reaction of the invention can be used to prepare such compounds as illustrated in Scheme 13. A cyclization reaction of the invention can also be used to prepare the ketone- and diol-containing β-blockers Betagan® (255) and Corgard® (257).

A cyclization reaction of the invention can also be used to prepare CellCept® (II-F) as illustrated in Scheme 14. First introduced in 1995 by Hoffmann La-Roche, CellCept® (II-F) is an immunosuppressant agent widely used by organ transplant patients. It is currently in multiple clinical trials for a wide variety of additional indications. Worldwide annual sales of CellCept® often exceed $1B.

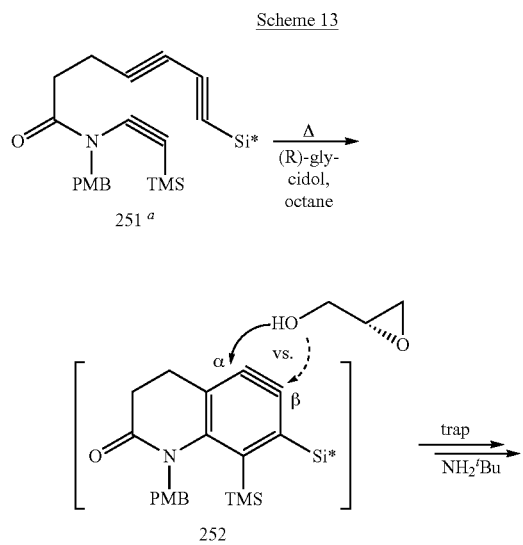

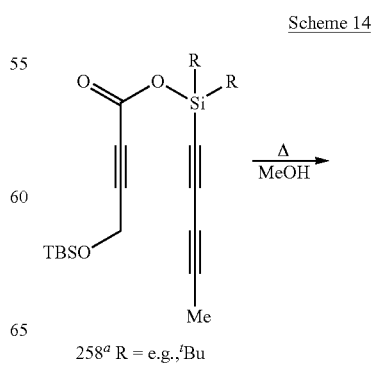

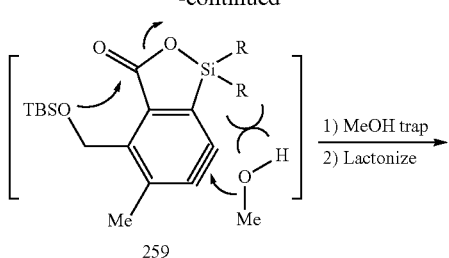

259

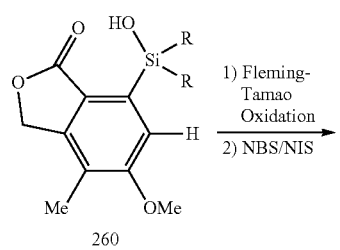

260

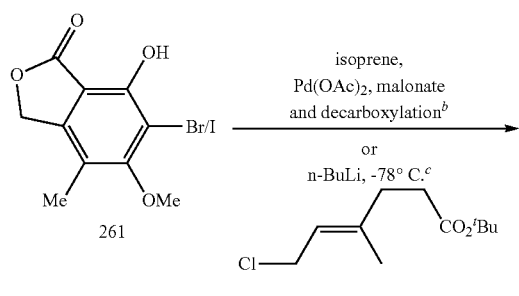

261

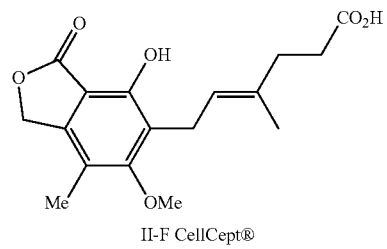

II-F CellCept®

The invention will now be illustrated by the following non-limiting Examples.

EXAMPLES

The following reactions that illustrate the methods of the invention were carried out under the conditions shown.

Example 1

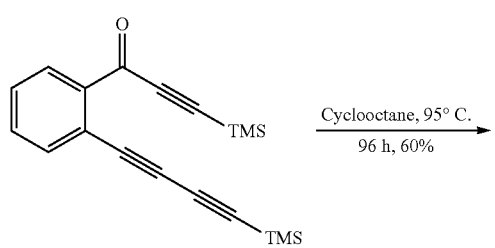

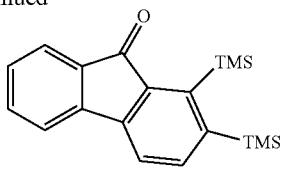

Spectral Data for Product of Example 1

1,2-Bis(trimethylsilyl)-9H-fluoren-9-one $^1$H NMR (500 MHz, CDCl$_3$): δ=7.72 (d, J=7.51 Hz, 1H), 7.60 (ddd, J=1.0, 1.0, 7.3 Hz, 1H), 7.50 (ddd, J=1.0, 1.0, 7.4, 1H), 7.46 (ddd, J=1.2, 7.3, 7.3 Hz, 1H), 7.45 (d, J=7.5 Hz, 1H), 7.28 (ddd, 1.3, 7.3, 7.3 Hz, 1H), 0.44 [s, Si(CH$_3$)$_3$], and 0.39 [s, Si(CH$_3$)$_3$]. GC-MS t$_r$=11.44 min; m/z: 324, 309, 251, 147, and 73.

Example 2

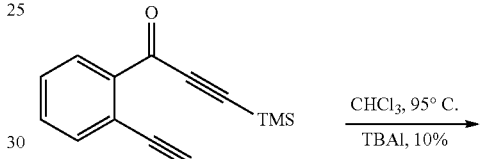

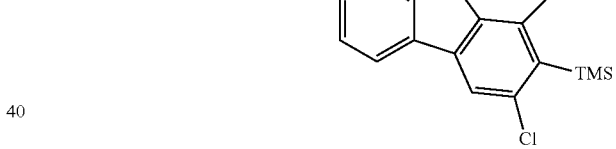

Spectral Data for Product of Example 2

3-Chloro-1,2-bis(trimethylsilyl)-9H-fluoren-9-one $^1$H NMR (500 MHz, CDCl$_3$): δ=8.17, (ddd, J=0.9, 0.9, 7.6 Hz, 1H), 7.65 (ddd, J=1.0, 1.1, 7.3 Hz, 1H), 7.61 (s, 1H), 7.52 (ddd, J=1.2, 7.6, 7.6 Hz, 1H), 7.34 (ddd, J=1.0, 7.5, 7.5 Hz, 1H), 0.42 [s, Si(CH$_3$)$_3$], and 0.40 [s, Si(CH$_3$)$_3$]. GC-MS t$_r$=11.91 min; m/z: 345, 343, 287, 250, 164, and 73.

Example 3

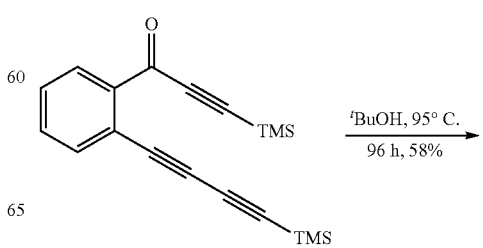

-continued

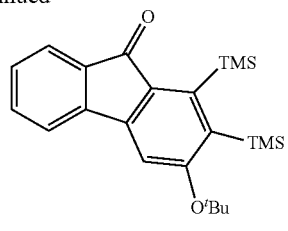

Spectral Data for Product of Example 3

3-(tert-Butoxy)-1,2-bis(trimethylsilyl)-9H-fluoren-9-one $^1$H NMR (500 MHz, CDCl$_3$): δ=7.55 (ddd, J=1.0, 1.0, 7.3 Hz, 1H), 7.42 (d, J=1.1 Hz, 1H), 7.42 (dd, J=1.1, 1.1 Hz, 1H), 7.26 (nfom, 2H), 7.04 (s, 1H), 1.61 [s, C(CH$_3$)$_3$], 0.40 [s, Si(CH$_3$)$_3$], and 0.35 [s, Si(CH$_3$)$_3$]. $^{13}$C NMR (125 MHz, CDCl$_3$): δ=194.4, 166.9, 155.1, 146.8, 143.4, 141.7, 135.3, 133.9, 133.8, 129.3, 123.6, 119.5, 107.2, 79.9, 29.3, 3.2, and 2.9. GC-MS t$_r$=12.55 min; m/z: 396, 340, 325, 309, 279, 267, 250, 235, 73, and 57.

Example 4

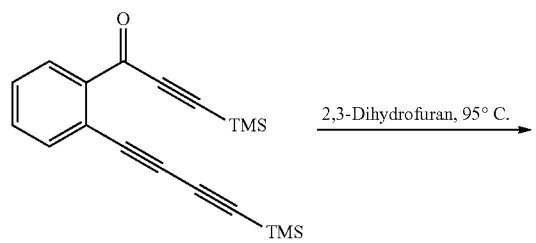

Spectral Data for Product of Example 4

4,5-Bis(trimethylsilyl)-3,3a-dihydro-2H-fluoreno[3',4':3,4]cyclobuta[1,2-b]furan-6(10dH)-one GC-MS t$_r$=14.50 min; m/z: 392, 377, 349, 319, 303, 289, 275, 215, and 73.

Example 5

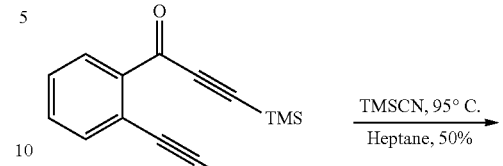

Spectral Data for Product of Example 5

9-Oxo-1,2-bis(trimethylsilyl)-9H-fluorene-3-carbonitrile $^1$H NMR (500 MHz, CDCl$_3$): δ=7.72 (s, 1H), 7.66 (ddd, J=1.0, 1.0, 7.4 Hz, 1H), 7.55 (nfom, 1H), 7.54 (nfom, 1H) 7.37, (nfom), 0.54 [s, Si(CH$_3$)$_3$], and 0.42 [s, Si(CH$_3$)$_3$]. $^{13}$C NMR (125 MHz, CDCl$_3$): δ=195.0, 157.4, 153.9, 143.3, 143.0, 142.6, 135.3, 133.6, 130.3, 124.6, 124.4, 123.3, 120.8, 120.3, 2.8, and 2.4. GC-MS t$_r$=13.63 min; m/z: 349, 334, 318, 276, 260, 159, and 73.

Example 6

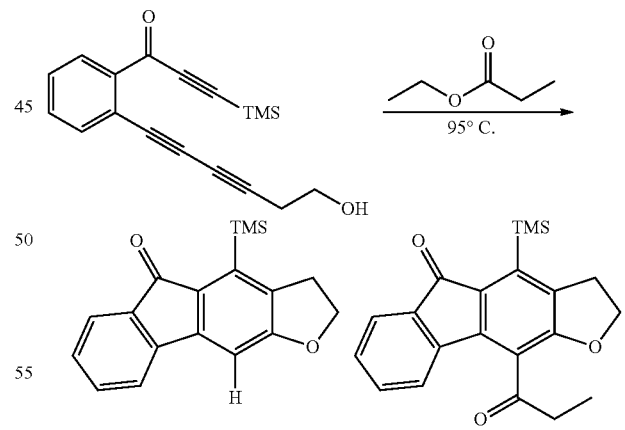

Spectral Data for the Products of Example 6

4-(Trimethylsilyl)-2H-fluoreno[3,2-b]furan-5(3H)-one and 10-Propionyl-4-(trimethylsilyl)-2H-fluoreno[3,2-b]furan-5(3H)-one Spectral data for proton-trapped product: $^1$H NMR (500 MHz, CDCl$_3$): δ=7.53 (dd, J=7.3 0.7 Hz, ArHCC=O), 7.42

(ddd, J=7.3, 7.3, 1.0 Hz, ArH), 7.39 (dd, J=6.2, 0.9 Hz, ArH) 7.25 (ddd, J=7.2, 7.2, 1.3 Hz, ArH), 6.92 (s, ArHCOCH$_2$), 4.63 (t, J=8.5 Hz, CH$_2$O), and 3.27 (t, J=8.5 Hz, CH$_2$CH$_2$O), and 0.40 [s, Si(CH$_3$)$_3$]. HR ESI-MS: C$_{18}$H$_{18}$O$_2$Si [M+Na]$^+$ requires 317.0968. found 317.0980. Spectral Data for propionate-trapped product: $^1$H NMR (500 MHz, CDCl$_3$): δ=7.55 (d, J=7.0 Hz, ArHCC=O), 7.38-7.43 (m, 1H), 7.35, (ddd, J=7.6, 7.6, 1.2 Hz, 1H), 7.23 (dd, J=6.9, 0.9, 0.9 Hz, 1H), 4.66 (t, J=8.8, CH$_2$CH$_2$OC), 3.29 (t, J=8.5 Hz, CH$_2$CH$_2$OC), 2.98 (q, J=7.2 Hz, CH$_2$CH$_3$), 1.26 (t, J=7.2 Hz, CH$_2$CH$_3$) and 0.40 [Si(CH$_3$)$_3$]. GC-MS t$_r$=13.17 min; m/z: 350, 335, 317, 278, 235, 220, 189, and 153.

Example 7

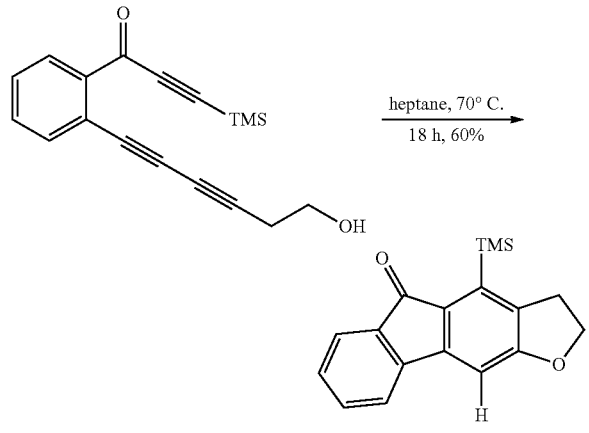

Spectral Data for the Product of Example 7

4-(Trimethylsilyl)-2H-fluoreno[3,2-b]furan-5(3H)-one $^1$H NMR (500 MHz, CDCl$_3$): δ=7.53 (dd, J=7.3 0.7 Hz, ArHCC=O), 7.38-7.44 (m, 2H), 7.25 (ddd, J=7.2, 7.2, 1.3 Hz, ArH), 6.92 (s, ArHCOCH$_2$), 4.63 (t, J=8.8 Hz, CH$_2$O), and 3.27 (t, J=8.8 Hz, CH$_2$CH$_2$O), and 0.40 [s, Si(CH$_3$)$_3$]. HR ESI-MS: C$_{18}$H$_{18}$O$_2$Si [M+Na]$^+$ requires 317.0968. found 317.0980.

Example 8

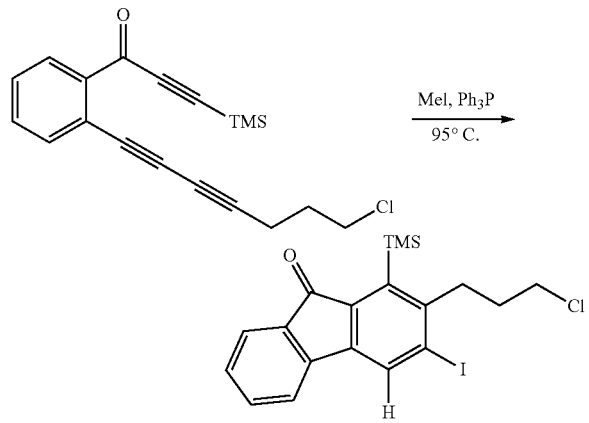

Spectral Data for the Product of Example 8

2-(3-Chloropropyl)-3-iodo-1-(trimethylsilyl)-9H-fluoren-9-one $^1$H NMR (500 MHz, CDCl$_3$): δ 8.08 (s, CHCl), 7.60 (d, J=7.3 Hz, CHCC=O), 7.47 (ddd, J=7.4, 6.7, 1.1 Hz, ArH), 7.30 (dd, J=7.3, 7.3 Hz, ArH), 3.64 (t, J=6.7 Hz, CH$_2$CH$_2$CH$_2$Cl), 3.18 (bt, J=8.3 Hz, CH$_2$CH$_2$CH$_2$Cl), 1.95 (bp, J=6.7 Hz, CH$_2$CH$_2$CH$_2$Cl), and 0.50 [s, Si(CH$_3$)$_3$]. HR ESI-MS: C$_{19}$H$_{20}$ClIOSi [M+Na]$^+$ requires 476.9909. found 476.9960. GC-MS t$_r$=14.03 min; m/z: 454, 439, 403, 275, 261, 235, 217, 189, 163, and 73.

Example 9

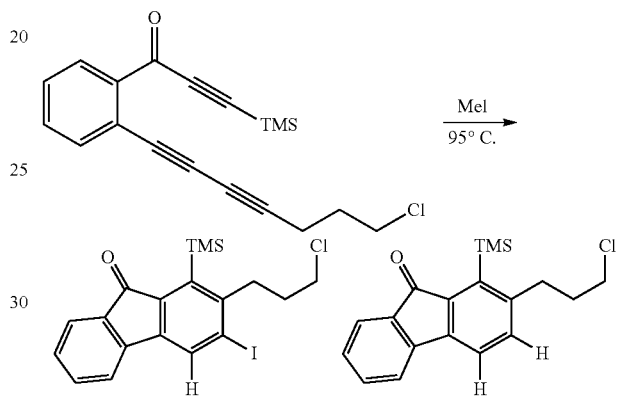

Spectral Data for the Product of Example 9

2-(3-Chloropropyl)-3-iodo-1-(trimethylsilyl)-9H-fluoren-9-one

GC-MS t$_r$=14.03 min; m/z: 454, 439, 403, 275, 261, 235, 217, 189, 163, and 73. GC-MS t$_r$=12.24 min; m/z: 328, 313, 277, 250, 235, 221, 203, 189, 165, 139, and 73.

Example 10

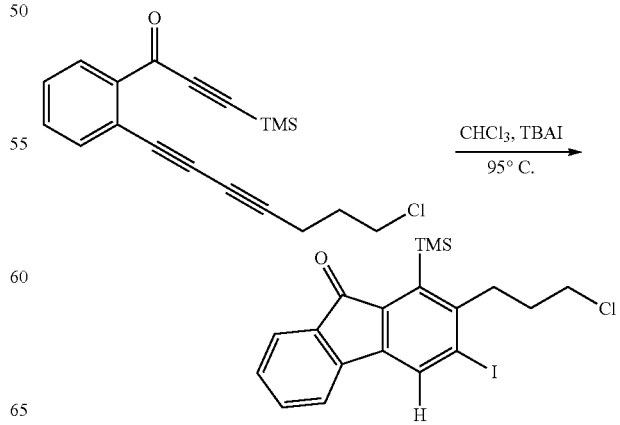

Spectral Data for the Product of Example 10

2-(3-Chloropropyl)-3-iodo-1-(trimethylsilyl)-9H-fluoren-9-one $^1$H NMR (500 MHz, CDCl$_3$): δ=8.08 (s, CHCl), 7.60 (d, J=7.3 Hz, CHCC=O), 7.47 (ddd, J=7.4, 6.7, 1.1 Hz, ArH), 7.30 (dd, J=7.3, 7.3 Hz, ArH), 3.64 (t, J=6.7 Hz, CH$_2$CH$_2$CH$_2$Cl), 3.18 (bt, J=8.3 Hz, CH$_2$CH$_2$CH$_2$Cl), 1.95 (bp, J=6.7 Hz, CH$_2$CH$_2$CH$_2$Cl), and 0.50 [s, Si(CH$_3$)$_3$]. GC-MS t$_r$=14.03 min; m/z: 454, 439, 403, 275, 261, 235, 217, 189, 163, and 73.

Example 11

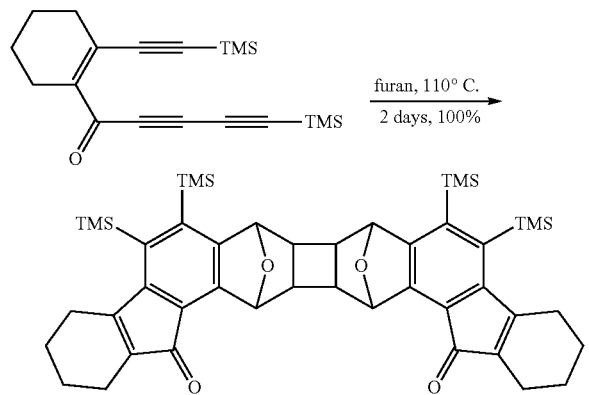

Spectral Data for the Product of Example 11

5,6,9,10-Tetrakis(trimethylsilyl)-1,2,3,4,7,7a,7b,8,11,12,13,14,16,16a,16b,17-hexadecahydro-7,17:8,16-diepoxybiphenyleno[2,3-a:7,6-a']difluorene-15,18-dione $^1$H NMR (500 MHz, CDCl$_3$): δ=4.73 (dd, J=3.5, 1.0 Hz, 1H), 4.24 (d, J=3.5 Hz, 1H), 3.00 (t, J=2.5 Hz, 1H), 2.48 (nfom, C=C(CH$_2$)—C=O), 2.28 (nfom, CH$_2$C=C—C=O), 2.22 (dd, J=3.5, 2.5 Hz, 1H), 1.77 (m, CH$_2$CH$_2$CH$_2$CH$_2$), 1.69 (m, CH$_2$CH$_2$CH$_2$CH$_2$), 0.23 (s, Si(CH$_3$)$_3$), and 0.07 (s, Si(CH$_3$)$_3$). LC-MS: t$_r$=4.10; [M+Na]$^+$: 811.0

Example 12

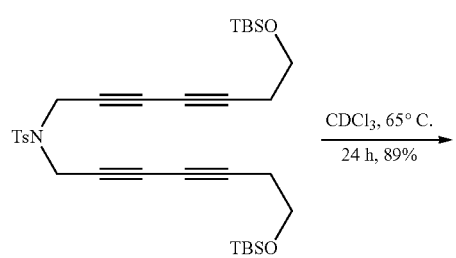

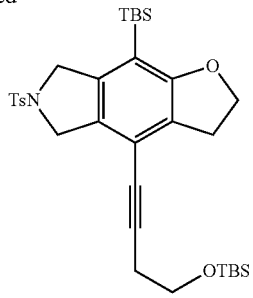

Spectral Data for the Product of Example 12

8-(tert-Butyldimethylsilyl)-4-(4-((tert-butyldimethylsilyl)oxy)but-1-yn-1-yl)-6-tosyl-3,5,6,7-tetrahydro-2H-furo[2,3-f]isoindole $^1$H NMR (500 MHz, CDCl$_3$): δ=7.74 (d, J=8.0 Hz, Ar—H), 7.30 (d, J=8.0 Hz, Ar—H), 4.56 (s, 2H), 4.53 (s, 2H), 4.45 (t, J=8.5 Hz, ArOCH$_2$), 3.80 (t, J=7.0 Hz, OCH$_2$CH$_2$—C), 3.11 (t, J=8.5 Hz, ArCH$_2$CH$_2$O), 2.66 (t, J=7.0 Hz, OCH$_2$CH$_2$—C), 2.40 (s, Ar—CH$_3$), 0.92 (s, C(CH$_3$)$_3$), 0.82 (s, C(CH$_3$)$_3$), 0.27 (s, tBuSi(CH$_3$)$_2$), 0.10 (s, tBuSi(CH$_3$)$_2$). LC-MS: t$_r$=9.31 min; [M+H]$^+$: 612.1

Example 13

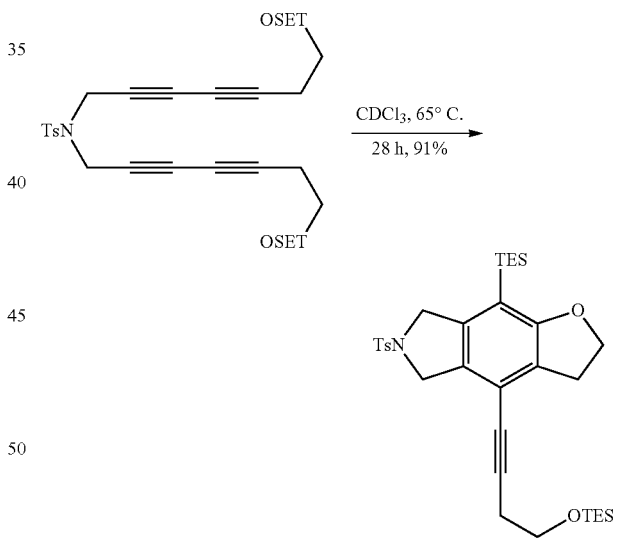

Spectral Data for Product of Example 13

8-(Triethylsilyl)-4-(4-((triethylsilyl)oxy)but-1-yn-1-yl)-6-tosyl-3,5,6,7-tetrahydro-2H-furo[2,3-f]isoindole $^1$H NMR (500 MHz, CDCl$_3$): δ=7.76 (d, J=8.0 Hz, Ar—H), 7.31 (d, J=8.0 Hz, Ar—H), 4.55 (s, 2H), 4.53 (s, 2H), 4.47 (t, J=8.5 Hz, ArOCH$_2$), 3.80 (t, J=7.0 Hz, OCH$_2$CH$_2$—C), 3.11 (t, J=8.5 Hz, ArCH$_2$CH$_2$O), 2.67 (t, J=7.0 Hz, OCH$_2$CH$_2$—C), 2.40 (s, Ar—CH$_3$), 0.99 (t, J=8.0

Hz, Si—CH$_2$CH$_3$), 0.87 (t, J=8.0 Hz, Si—CH$_2$CH$_3$), 0.78 (t, J=8.0 Hz, Si—CH$_2$CH$_3$), 0.64 (t, J=8.0 Hz, Si—CH$_2$CH$_3$),

Example 14

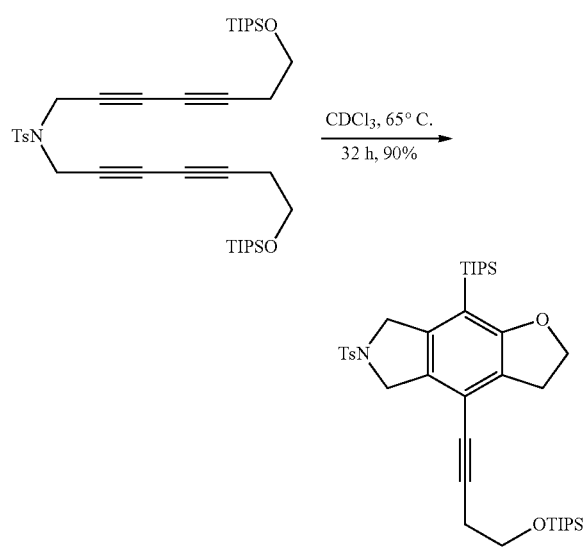

Spectral Data for the Product of Example 14

8-(Triisopropylsilyl)-4-(4-((triisopropylsilyl)oxy)but-1-yn-1-yl)-6-tosyl-3,5,6,7-tetrahydro-2H-furo[2,3-]isoindole $^1$H NMR (500 MHz, CDCl$_3$): δ=7.75 (d, J=8.0 Hz, Ar—H), 7.29 (d, J=8.0 Hz, Ar—H), 4.65 (s, 2H), 4.53 (s, 2H), 4.42 (t, J=8.5 Hz, ArOCH$_2$), 3.87 (t, J=7.0 Hz, OCH$_2$CH$_2$—C), 3.10 (t, J=8.5 Hz, ArCH$_2$CH$_2$O), 2.69 (t, J=7.0 Hz, OCH$_2$CH$_2$—C), 2.40 (s, Ar—CH$_3$), 1.45 (septet, CHMe$_2$), 1.10 (s, CH(CH$_3$)$_2$), 1.05 (s, CH(CH$_3$)$_2$). LC-MS: t$_r$=19.24 min; [M+H]$^+$: 696.1

Example 15

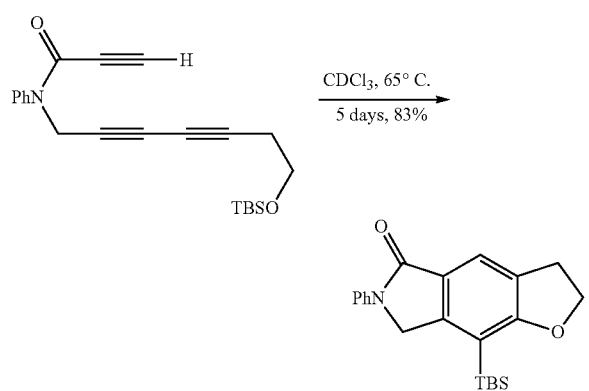

Spectral Data for the Product of Example 15

8-(tert-Butyldimethylsilyl)-2,3,6,7-tetrahydro-6-phenylfuro[2,3-f]isoindol-5-one $^1$H NMR (500 MHz, CDCl$_3$): δ=7.85 (s, Ar—H), 7.84 (s, Ar—H), 7.71 (s, Ar—H), 7.42 (d, J=7.5 Hz, Ar—H), 7.42 (d, J=7.5 Hz, Ar—H), 7.15 (td, J=7.5, 1.0 Hz, Ar—H), 4.76 (s, ArCH$_2$N), 4.60 (t, J=9.0 Hz, OCH$_2$), 3.25 (t, J=9.0 Hz, ArCH$_2$CH$_2$O), 0.92 (s, C(CH$_3$)$_3$), 0.42 (s, tBuSi(CH$_3$)$_2$. LC-MS: t$_r$=3.40 min; [M+NH$_4$]$^+$: 383.2

Example 16

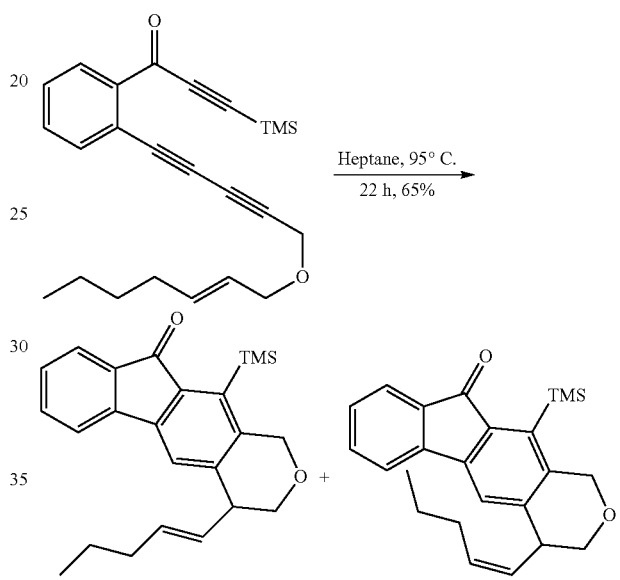

E:Z = ca. 2:1

Spectral Data for Products of Example 16

(E)-4-(Pent-1-en-1-yl)-11-(trimethylsilyl)-3,4-dihydroindeno[1,2-g]isochromen-10(1H)-one $^1$H NMR (500 MHz, CDCl$_3$): δ=7.58 (ddd, J=1.0, 1.0, 7.3 Hz, 1H), 7.46 (nfom), 7.45 (nfom), 7.37 (d, J=0.8 Hz, 1H), 7.26 (nfom), 5.73 (dddd, J=0.8, 6.8, 6.8, 15.3 Hz, 1H), 5.46 (dddd, J=1.4, 1.4, 8.8, 15.2 Hz, 1H), 4.88 (d, J=1.3 Hz, 2H), 3.97 (dd, J=5.3, 11.1 Hz, 1H) 3.66 (dd, J=7.1, 11.1 Hz, 1H), 3.55 (nfom, 1H), 2.09 (ddd, 1.5, 7.0, 7.0 Hz, 1H), 2.07 (ddd, J=1.5, 6.8, 6.8 Hz, 1H), 1.46 (sextet, J=7.4 Hz, 2H), 0.95 (t, J=7.4 Hz, 3H), and 0.42 [s, Si(CH$_3$)$_3$]. GC/MS t$_r$=13.59 min; m/z: 376, 361, 331, 306, 287, 202, 189, 137, and 73.

(Z)-4-(Pent-1-en-1-yl)-11-(trimethylsilyl)-3,4-dihydroindeno[1,2-g]isochromen-10(1H)-one: $^1$H NMR (500 MHz, CDCl$_3$): δ=7.58 (ddd, J=1.0, 1.0, 7.3 Hz, 1H), 7.45 (nfom), 7.44 (nfom), 7.32 (d, J=0.7 Hz, 1H), 7.26 (nfom), 5.71 (dddd, J=0.8, 7.5, 7.5, 10.8 Hz, 1H), 5.38 (dddd, J=1.7, 1.7, 9.3, 10.8 Hz, 1H), 4.93 (d, J=15.1 Hz, 1H), 4.87 (dd, J=1.28 Hz, 1H), 3.99 (nfom), 3.53 (nfom), 2.26 (??, 1H), 1.53 (??, 1H), 1.02 (t, J=7.4 Hz, 3H), and 0.42 [s, Si(CH$_3$)$_3$]. GC-MS t$_r$=13.68 min; m/z: 376, 361, 331, 287, 215, 202, and 73.

Example 17

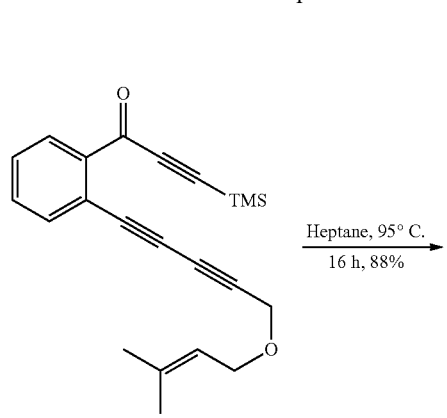

Spectral Data for Product of Example 17

4-(Prop-1-en-2-yl)-11-(trimethylsilyl)-3,4-dihydroindeno[1,2-g]isochromen-10(1H)-one ¹H NMR (500 MHz, CDCl₃): δ=7.59 (ddd, J=1.0, 1.0, 7.3 Hz, 1H), 7.48 (ddd, J=0.9, 1.6, 7.5 Hz, 1H), 7.45 (ddd, J=1.2, 7.4, 7.4 Hz, 1H) 7.33 (d, J=0.7 Hz, 1H), 7.26 (ddd, J=1.5, 7.2, 7.2 Hz, 1H), 5.03 (dq, J=2.1, 1.5 Hz, 1H), 4.91 (dq, J=0.8, 2.9 Hz, 1H), 4.90 (dd, J=1.2, 15.2 Hz, 1H), 4.85 (dd, J=1.3, 15.2 Hz, 1H), 3.97 (dd, J=5.5, 11.3 Hz, 1H), 3.84 (dd, J=6.0, 11.3 Hz, 1H), 3.63 (ddq, J=5.7, 5.7, 0.8 Hz, 1H), 1.72 (dd, J=0.9, 1.5 Hz, CCH₃), and 0.43 [s, Si(CH₃)₃]. ¹³C NMR (125 MHz, CDCl₃): δ=195.1, 145.9, 144.0, 143.1, 142.2, 140.5, 134.6, 134.2, 128.9, 124.0, 122.1, 119.8, 155.5, 71.2, 68.3, 47.8, 20.3, and 2.7. IR (neat): 2974, 2933, 2913, 2853, 2212, 1673, 1630, 1443, 1378, 1352, 1077, 1027, 1002, 925, and 897 cm⁻¹. GC-MS t$_r$=12.7 min; m/z: 348, 333, 303, 287, 277, 229, 215, 202, 189, 136, and 73. TLC: R$_f$ 0.4 (9:1 Hex/EtOAc)

Example 18

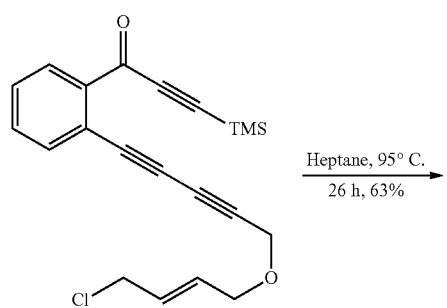

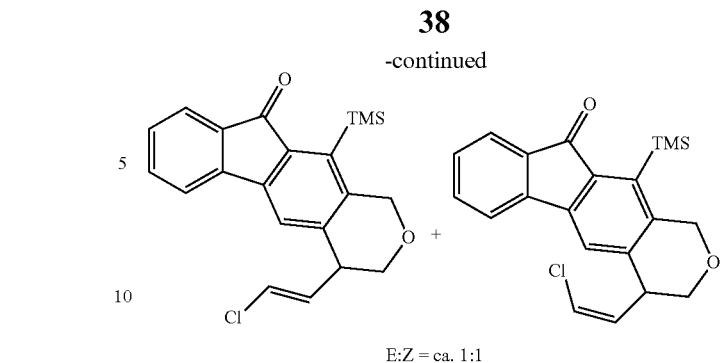

E:Z = ca. 1:1

Spectral Data for Products of Example 18

(E)-4-(2-Chlorovinyl)-11-(trimethylsilyl)-3,4-dihydroindeno[1,2-g]isochromen-10(1H)-one ¹H NMR (500 MHz, CDCl₃): δ=7.30 (ddd, J=0.9, 0.9, 7.4 Hz, 1H), 7.50 (nfom, 1H), 7.47 (nfom, 1H), 7.30 (s, 1H), 7.29 (nfom, 1H), 6.24 (d, J=13.3 Hz, 1H), 6.05 (dd, 9.2, J=13.3 Hz, 1H), 4.93 (d, J=15.6 Hz, 1H), 4.86 (dd, J=0.7, 15.6 Hz, 1H), 3.96 (dd, J=4.8, 11.1 Hz, 1H), 3.77 (dd, J=5.6, 11.2 Hz, 1H), 3.62 (nfom, 1H), and 0.42 [s, Si(CH₃)₃]. GC-MS t$_r$=13.48 min; m/z: 368, 353, 287, 257, 228, 202, 136, and 73. (Z)-4-(2-Chlorovinyl)-11-(trimethylsilyl)-3,4-dihydroindeno[1,2-g]isochromen-10(1H)-one: ¹H NMR (500 MHz, CDCl₃): δ=7.59 (ddd, J=1.0, 1.0, 7.3 Hz, 1H), 7.48 (nfom, 1H), 7.46 (nfom, 1H), 7.35 (s, 1H), 7.28 (nfom), 6.29 (d, J=7.1 Hz, 1H), 5.96 (dd, J=7.1, 9.7 Hz, 1H), 4.94 (d, J=15.3 Hz, 1H), 4.87 (d, J=15.3 Hz, 1H), 4.25 (nfom, 1H), 4.00 (dd, J=4.9, 11.3 Hz, 1H), 3.73 (dd, J=5.5, 11.3 Hz, 1H), and 0.42 [s, Si(CH₃)₃]. GC-MS t$_r$=13.52 min; m/z: 368, 353, 287, 257, 228, 202, 136, and 73.

Example 19

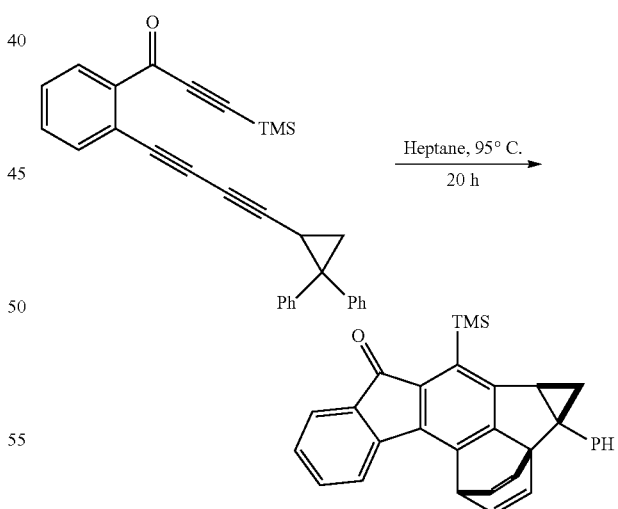

Spectral Data for Product of Example 19

(1S,3aR,3bR,4aS)-3b-Phenyl-5-(trimethylsilyl)-4,4a-dihydro-1H-1,3a-ethenocyclopropa[2,3]indeno[1,7-bc]fluoren-6(3bH)-one ¹H NMR (500 MHz, CDCl₃): δ=7.74 (d, J=7.5 Hz, 1H), 7.57 (d, J=7.4 Hz, 1H), 4.45 (nfom, 3H), 7.39 (nfom, 2H), 7.30 (dddd, J=1.3, 1.3, 7.3, 7.3 Hz, 1H), 7.22 (dd, J=7.4, 7.4 Hz, 1H), 7.06 (d, J=6.6 Hz, 1H), 6.90 (dd, J=5.8, 6.5 Hz, 1H), 6.73 (dd, J=5.5, 6.8 Hz, 1H), 6.69 (dd, J=1.4, 6.8 Hz, 1H), 5.50 (dddd, J=1.5, 1.5, 5.5, 5.5 Hz, 1H), 3.20 (dd, J=3.8, 8.3 Hz, 1H), 1.61 (dd, J=4.7, 8.2 Hz, 1H), 1.10 (dd, J=4.0, 4.5 Hz, 1H), and 0.45 [s, Si(CH$_3$)$_3$]. GC-MS t$_r$=16.02 min; m/z: 442, 427, 401, 365, 324, 313, 265, 162, and 73.

Example 20

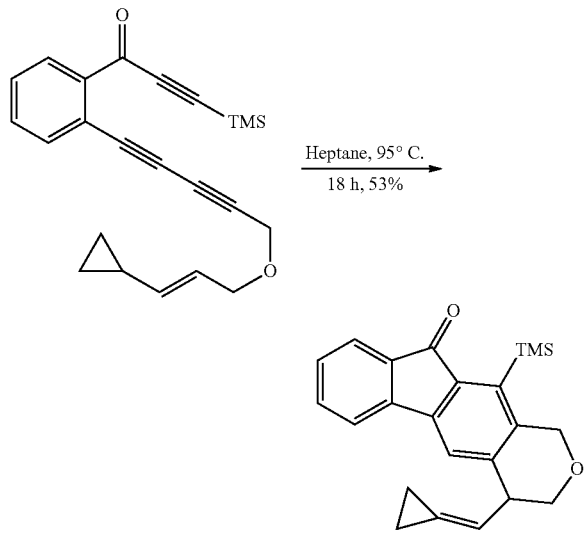

Spectral Data for Product of Example 20

4-(Cyclopropylidenemethyl)-11-(trimethylsilyl)-3,4-dihydroindeno[1,2-g]isochromen-10(1H)-one $^1$H NMR (500 MHz, CDCl$_3$): δ=7.58, (ddd, J=1.0, 1.0, 7.3 Hz, 1H), 7.48 (nfom, 1H), 7.44 (nfom, 1H), 7.31 (d, J=0.9 Hz, 1H), 7.26 (nfom, 1H), 5.88 (dtt, J=8.31, 2.0, 2.0 Hz, 1H), 4.93 (dd, J=1.4, 15.2 Hz, 1H), 4.89 (dd, J=1.5, 15.1 Hz, 1H), 4.00 (dd, J=5.0, 10.8 Hz, 1H), 3.83 (nfom, 1H), 3.77 (dd, J=6.7, 10.8 Hz, 1H), 1.26 (nfom, 1H), 0.88 (nfom, 1H), and 0.42 [s, Si(CH$_3$)$_3$]. GC-MS t$_r$=13.63 min; m/z: 360, 345, 330, 315, 301, 287, and 275.

Example 21

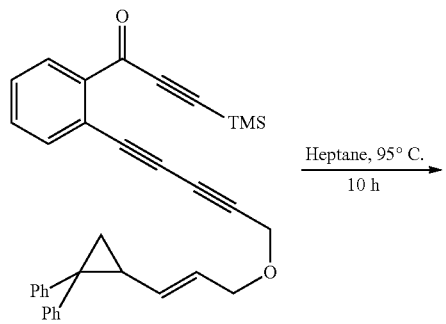

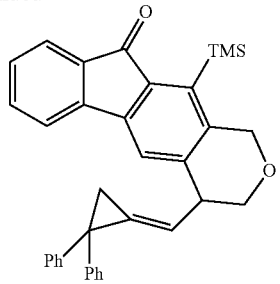

Spectral Data for Product of Example 21

(E)-4-((2,2-Diphenylcyclopropylidene)methyl)-11-(trimethylsilyl)-3,4-dihydroindeno[1,2-g]isochromen-10(1H)-one $^1$H NMR (500 MHz, CDCl$_3$): δ=7.82 (nfom, 1H), 7.80 (nfom, 1H), 7.60 (nfom, 1H), 7.54 (ddd, J=1.0, 1.0, 7.3 Hz, 1H), 7.49 (nfom, 2H), 7.40 (nfom, 6H), 7.31 (nfom, 4H), 7.25 (nfom, 1H), 7.23 (ddd, J=1.0, 7.3, 7.3 Hz, 1H), 6.95 (ddd, J=1.0, 1.0, 7.4 Hz, 1H), 4.92 (d, J=15.2 Hz), 4.88 (d, J=15.3 Hz, 1H), 4.07 (nfom, 1H), 3.80 (nfom, 1H), 2.31 (dd, J=2.0, 9.0 Hz, 1H), 1.85 (dd, J=2.1, 9.0 Hz, 1H) and 0.41 [s, Si(CH$_3$)$_3$]. GC-MS t$_r$=13.68 min; m/z: 376, 361, 331, 287, 275, 215, 202, 136, and 73.

Example 22

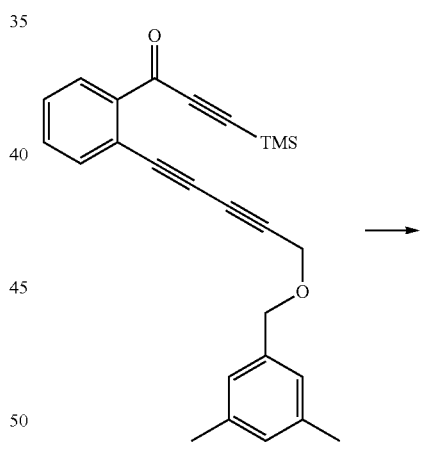

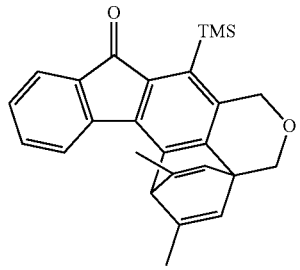

Spectral Data for Product of Example 22

$^1$H NMR (500 MHz, CDCl$_3$): δ=7.90 (d, J=7.5 Hz, 1H), 7.63 (d, J=7.0 Hz, 1H), 7.51 (dd, J=7.5, 7.5 Hz, 1H), 7.28

(dd, J=7.5, 7.5 Hz, 1H), 4.96 (s, 1H), 4.79 (br s, 2H), 4.39 (br s, 2H), 1.99 (br s, 6H), and 0.36 (br s, 9H). $^{13}$C NMR (125 MHz, CDCl$_3$): δ=194.3, 149.8, 148.8, 144.6, 142.4, 136.3, 136.0, 135.5, 135.1, 135.0, 134.4, 133.7, 128.3, 124.2, 121.8, 71.2, 70.4, 56.2, 51.2, 20.0, and 2.3 ppm. IR (neat): 2950, 2903, 2849, 1705, 1606, 1560, 1466, 1375, 1353, 1205, 1189, 1174, 1122, 1097, 995, and 942 cm$^{-1}$. HR ESI-MS: [C$_{26}$H$_{26}$O$_2$Si+Na]$^+$ requires 421.1594. found 421.1559.

Example 23

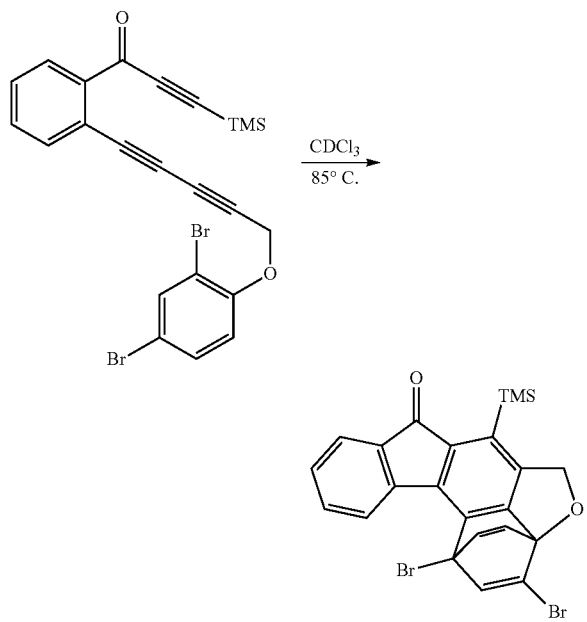

Spectral Data for Product of Example 23

$^1$H NMR (500 MHz, CDCl$_3$): δ=9.05 (d, J=8.0 Hz, 1H), 7.66 (ddd, J=8.0, 1.5, and 0.5 Hz, 1H), 7.51 (ddd, J=8.0, 8.0, and 1.5 Hz, 1H), 7.32 (ddd, J=7.5, 7.5, and 0.5 Hz, 1H), 6.97 (dd, J=7.0, and 0.5 Hz, 1H), 6.87 (br s, 1H), 6.80 (dd, J=7.0, and 1.0 Hz, 1H), 5.56 (d, J=13.0 Hz, 1H), 5.53 (d, J=13.0 Hz, 1H), and 0.34 (s, 9H).

Example 24

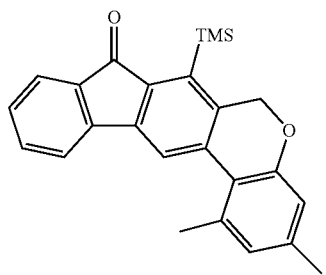

Spectral Data for Product of Example 24

$^1$H NMR (500 MHz, CDCl$_3$): δ=7.80 (s, 1H), 7.61 (ddd, J=7.0, 1.0, and 1.0 Hz, 1H), 7.51 (ddd, J=7.5, 1.5, and 1.0 Hz, 1H), 7.47 (ddd, J=7.5, 7.5, and 1.5 Hz, 1H), 7.29 (ddd, J=7.0, 7.0, and 1.5 Hz, 1H), 6.82 (br s, 1H), 6.74 (br s, 1H), 5.04 (br s, 2H), 2.67 (br s, 3H), 2.34 (br s, 3H) and 0.46 (s, 9H).

Example 25

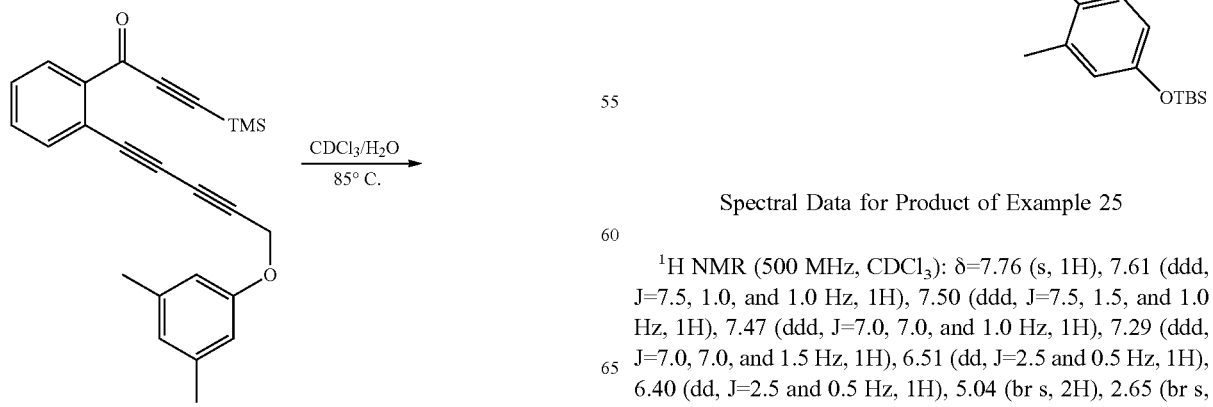

Spectral Data for Product of Example 25

$^1$H NMR (500 MHz, CDCl$_3$): δ=7.76 (s, 1H), 7.61 (ddd, J=7.5, 1.0, and 1.0 Hz, 1H), 7.50 (ddd, J=7.5, 1.5, and 1.0 Hz, 1H), 7.47 (ddd, J=7.0, 7.0, and 1.0 Hz, 1H), 7.29 (ddd, J=7.0, 7.0, and 1.5 Hz, 1H), 6.51 (dd, J=2.5 and 0.5 Hz, 1H), 6.40 (dd, J=2.5 and 0.5 Hz, 1H), 5.04 (br s, 2H), 2.65 (br s, 3H), 1.00 (s, 9H) and 0.45 (s, 9H).

Example 26

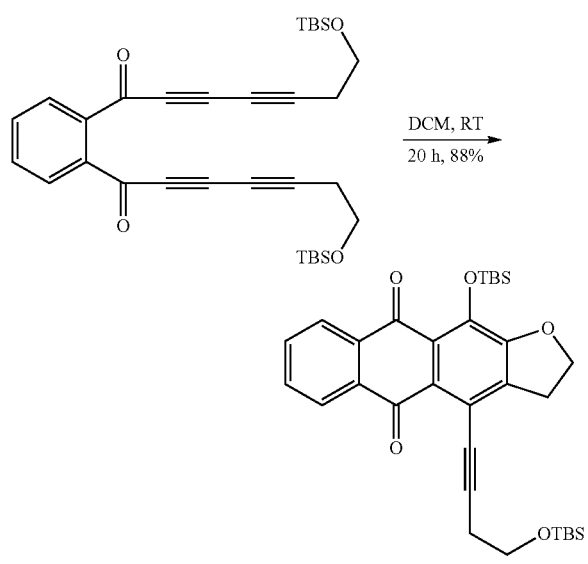

Spectral Data for the Product of Example 26

11-(tert-Butyldimethylsilyl)-4-(4-((tert-butyldimethylsilyl)oxy)but-1-yn-1-yl)-2,3-dihydroanthra[2,3-b]furan-5,10-dione $^1$H NMR (500 MHz, CDCl$_3$): δ=8.23 (dd, J=8.0, 1.0 Hz, Ar—H), 8.09 (dd, J=8.0, 1.0 Hz, Ar—H), 7.72 (dd, J=8.0, 1.5 Hz, Ar—H), 7.70 (dd, J=8.0, 1.5 Hz, Ar—H), 4.65 (t, J=9.0 Hz, ArOCH$_2$), 3.93 (t, J=7.5 Hz, OCH$_2$CH$_2$—C), 3.35 (t, J=9.0 Hz, ArCH$_2$CH$_2$O), 2.86 (t, J=7.5 Hz, OCH$_2$CH$_2$—C), 1.13 (s, C(CH$_3$)$_3$), 0.92 (s, C(CH$_3$)$_3$), 0.22 (s, tBuSi(CH$_3$)$_2$), 0.11 (s, tBuSi(CH$_3$)$_2$). LC-MS: t$_r$=9.97 min; [M+H]$^+$: 547.0

Example 27

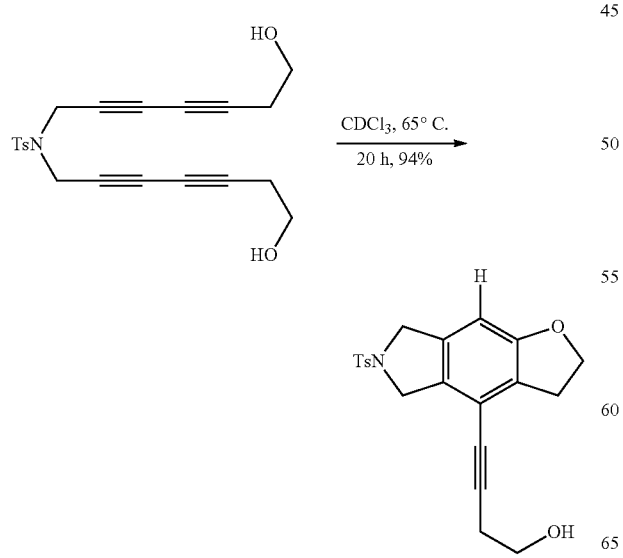

Spectral Data for the Product of Example 27

N,N-bis(7-Hydroxyhepta-2,4-diyn-1-yl)-4-methyl-benzenesulfonamide $^1$H NMR (500 MHz, CDCl$_3$): δ=7.74 (d, J=8.0 Hz, Ar—H), 7.30 (d, J=8.0 Hz, Ar—H), 6.45 (s, Ar—H), 4.54 (t, J=9.0 Hz, ArOCH$_2$), 4.52 (s, 2H), 4.49 (s, 2H), 3.80 (br t, J=6.5 Hz, HOCH$_2$), 3.14 (t, J=9.0 Hz, ArCH$_2$CH$_2$O), 2.70 (t, J=6.5 Hz, HOCH$_2$CH$_2$), 2.50 (t, J=6.5 Hz, OH), 2.38 (s, Ar—CH$_3$). LC-MS: t$_r$=3.05 min; [M+H]$^+$: 384.1

Example 28

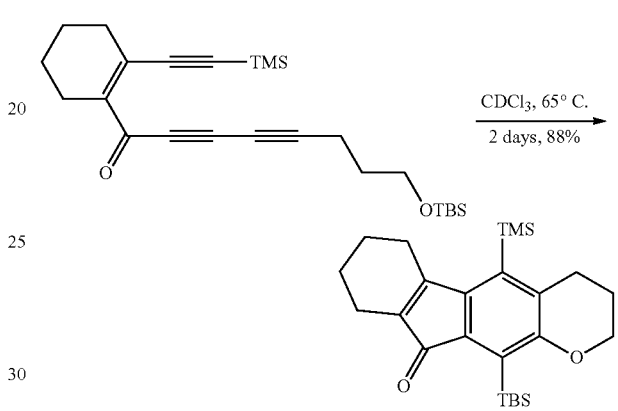

Spectral Data for the Product of Example 28

11-(tert-butyldimethylsilyl)-5-(trimethylsilyl)-3,4,6,7,8,9-hexahydroindeno[1,2-g]chromen-10(2H)-one $^1$H NMR (500 MHz, CDCl$_3$): δ=4.09 (t, J=5.5 Hz, CH$_2$O), 2.77 (t, J=5.5 Hz, ArCH$_2$), 2.57 [nfom, C═C(CH$_2$)—C═O], 2.22 (nfom, CH$_2$C═C—C═O), 1.90 (pentet, J=5.5 Hz, ArCH$_2$CH$_2$CH$_2$O), 1.70 (m, CH$_2$CH$_2$CH$_2$CH$_2$), 0.97 (s, C(CH$_3$)$_3$), 0.41 (s, Si(CH$_3$)$_3$), and 0.29 (s, tBuSi(CH$_3$)$_2$). LC-MS: t$_r$=8.35 min; [M+H$_3$O]$^+$: 443.2

Example 29

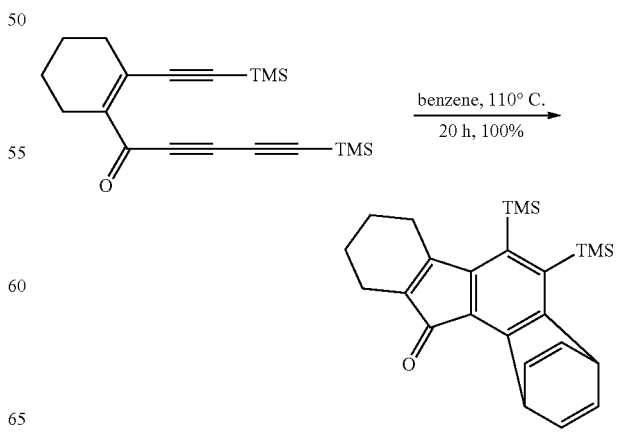

Spectral Data for the Product of Example 29

5,6-bis(trimethylsilyl)-7,8,9,10-tetrahydro-1H-1,4-ethenobenzo[a]fluoren-11(4H)-one $^1$H NMR (500 MHz, CDCl$_3$): δ=6.75 (m, HC=CH), 5.99 (nfom, 1H), 5.11 (nfom, 1H), 2.59 [nfom, C=C(CH$_2$)—C=O], 2.25 (nfom, CH$_2$C=C—C=O), 1.71 (m, CH$_2$CH$_2$CH$_2$CH$_2$), 0.42 (s, Si(CH$_3$)$_3$), and 0.31 (s, Si(CH$_3$)$_3$). LC-MS: t$_r$=6.57 min; [M+H]$^+$: 405.1

Example 30

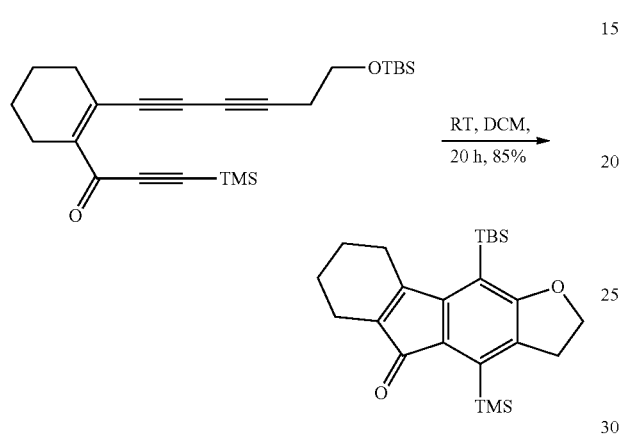

Spectral Data for the Product of Example 30

10-(tert-butyldimethylsilyl)-2,3,6,7,8,9-hexahydro-4-(trimethylsilyl)fluoreno[3,2-b]furan-5-one $^1$H NMR (500 MHz, CDCl$_3$): δ=4.42 (t, J=8.9 Hz, CH$_2$O), 3.15 (br t, J=8.9 Hz, ArCH$_2$), 2.49 [nfom, C=C(CH$_2$)—C=O], 2.23 (nfom, CH$_2$C=C—C=O), 1.69 (m, CH$_2$CH$_2$CH$_2$CH$_2$), 0.98 [s, C(CH$_3$)$_3$], 0.36 [s, tBuSi(CH$_3$)$_2$], and 0.36 [s, Si(CH$_3$)$_3$]. $^{13}$C NMR (125 MHz, CDCl$_3$): δ=198.2 (C=O), 169.1, 157.6, 154.9, 136.2, 133.9, 130.6, 128.2, 70.2 (CH$_2$O), 31.3, 28.1 SiC(Me)$_3$, 27.5, 23.2, 21.5, 20.2, 18.9 (CMe$_3$), 1.6, and 1.4. LC-MS: t$_r$=8.86 min; [M+H]$^+$: 413.2

Example 31

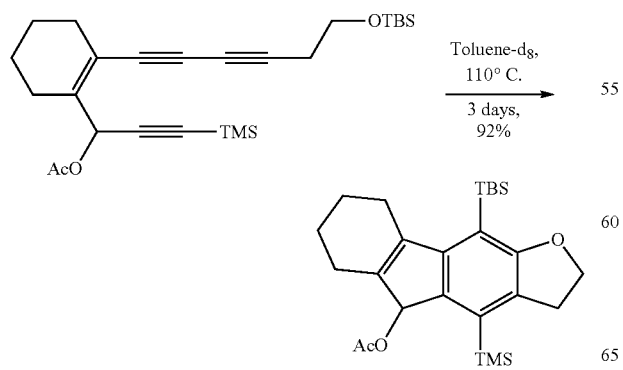

Spectral Data for the Product of Example 31

10-(tert-butyldimethylsilyl)-4-(trimethylsilyl)-3,5,6,7,8,9-hexahydro-2H-fluoreno[3,2-b]furan-5-yl acetate LC-MS: t$_r$=12.6 min; [M-OAc]$^+$: 397.0

Example 32

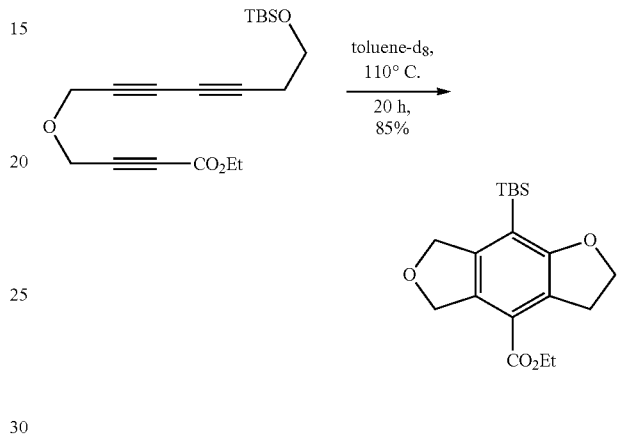

Spectral Data for the Product of Example 32

Ethyl 8-(tert-butyldimethylsilyl)-2,3,5,7-tetrahydrobenzo[1,2-b:4,5-c']difuran-4-carboxylate $^1$H NMR (500 MHz, toluene-d8): δ=5.42 (t, J=2.0 Hz, 2H), 5.08 (br s, 2H), 4.02 (t, J=9.0 Hz, OCH$_2$CH$_2$), 3.96 (q, J=7.5 Hz, OCH$_2$CH$_3$), 3.10 (t, J=9.0 Hz, OCH$_2$CH$_2$), 0.96 (t, J=7.5 Hz, OCH$_2$CH$_3$) 1.77 (m, CH$_2$CH$_2$CH$_2$CH$_2$), 1.69 (m, CH$_2$CH$_2$CH$_2$CH$_2$), 0.90 (s, C(CH$_3$)$_3$), and 0.26 (s, tBuSi(CH$_3$)$_2$). LC-MS: t$_r$=5.35 min; [M+H]$^+$: 349.0

Example 33

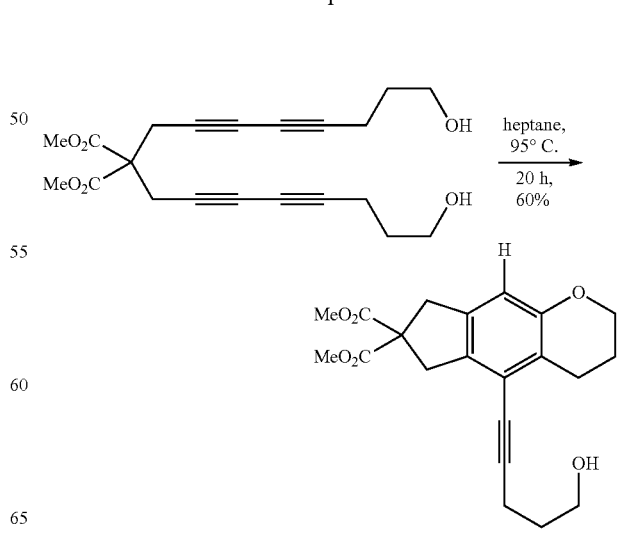

Spectral Data for the Product of Example #33

Dimethyl 5-(5-Hydroxypent-1-yn-1-yl)-3,4,6,8-tetrahydrocyclopenta[g]chromene-7,7(2H)-dicarboxylate ¹H NMR (500 MHz, CDCl₃): δ=6.59 (s, ArH), 4.09 (bt, J=5.1 Hz, CH₂OC), 3.84 (t, J=6.2 Hz, CH₂OH), 3.75 (s, CO₂CH₃), 3.56 (s, C(CO₂Me)₂CH₂) 3.52 (bs, C(CO₂Me)₂CH₂), 2.79 (bt, J=6.6 Hz, CCH₂CH₂CH₂OC), 2.60 (t, J=6.9 Hz, CH₂CH₂CH₂OH) 1.97 (bp, J=6.5 Hz, CCH₂CH₂CH₂OC), and 1.88 (tt, J=6.7, 6.4 Hz, CH₂CH₂CH₂OH). ¹³C NMR (500 MHz, CDCl₃): δ=172.2, 154.3, 138.2, 134.2, 122.5, 119.8, 112.2, 97.5, 66.1, 61.8, 59.9, 53.0, 40.8, 40.1, 31.7, 23.9, 22.2, and 16.3. IR (neat): 3458, 2951, 2876, 2229, 1734, 1604, 1587, 1436, 1341, 1253, 1199, 1174, 1160, 1132, 1104, and 1060 cm⁻¹. HR ESI-MS: $C_{21}H_{24}O_6$ [M+Na]⁺ requires 395.1465. found 395.1461

Example 34

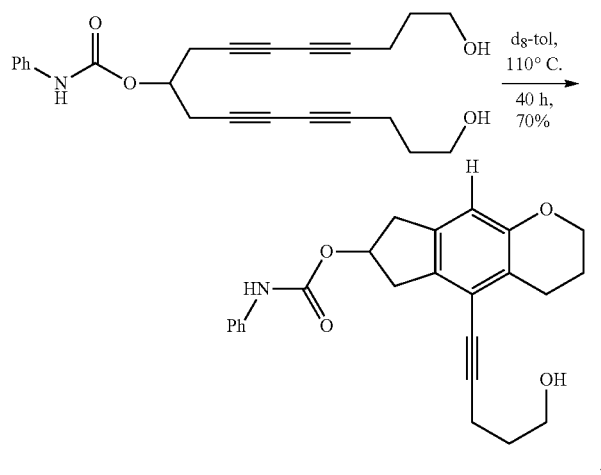

Spectral Data for the Product of Example 34

5-(5-hydroxypent-1-yn-1-yl)-2,3,4,6,7,8-hexahydrocyclopenta[g]chromen-7-yl phenylcarbamate ¹H NMR (500 MHz, CDCl₃): δ=7.28-7.38 (m, 4H), 7.05 (tt, J=7.4 and 1.2 Hz, 1H), 6.67 (s, CHCO), 6.56 (bs, NH), 5.55 (dddd, J=6.1, 6.1, 2.4, 2.4 Hz, CHOC=O), 4.12 (bt, J=5.0 Hz, CH₂CH₂CH₂OC), 3.84 (t, J=6.2 Hz, CH₂CH₂CH₂OH), 3.277 (dd, J=17.0, 5.8 Hz, CH$_a$CHOC), 3.275 (dd, J=17.0, 5.8 Hz, CH$_b$CHOC), 3.08 (dd, J=17.3, 2.2 Hz, CH$_a$CC$_{ar}$H) 3.03 (dd, J=17.0, 2.3, CH$_b$CC$_{ar}$H), 2.83 (bt, J=6.5 Hz, CH₂CH₂CH₂OC), 2.60 (t, J=6.9, CH₂CH₂CH₂OH), 2.00 (bp, J=6.5 Hz, CH₂CH₂CH₂OC), and 1.88 (t, J=6.8, 6.2 Hz, CH₂CH₂CH₂OH). GC-MS t$_r$=11.42 min; m/z: 413, 371, 295, 267, 251, 235, 207, 191, 149, 103, and 59. HR ESI-MS: $C_{24}H_{25}NO_4$ [M+Na]⁺ requires 414.1676. found 414.1716.

Example 35

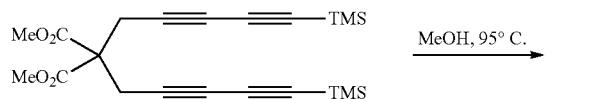

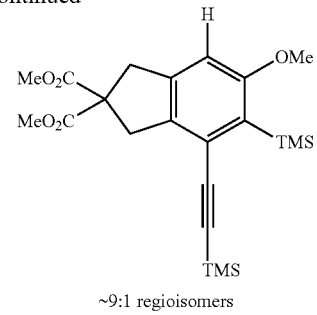

~9:1 regioisomers

Spectral Data for the Product of Example 35

Dimethyl 6-Methoxy-5-(trimethylsilyl)-4-((trimethylsilyl)ethynyl)-1H-indene-2,2(3H)-dicarboxylate ¹H NMR (500 MHz, CDCl₃): δ=6.66 (s, ArH), 3.76 (s, CO₂CH₃), 3.72 (s, OCH₃), 3.59 (s, CH₂CCC≡C), 3.58 (s, CH₂CC$_{aryl}$H), 0.35 (s, C$_{aryl}$Si(CH₃)₃), and 0.24 (s, C≡CSi(CH₃)₃). LC-MS t$_r$=5.38 min; [M+1]⁺: 433.0

Example 36

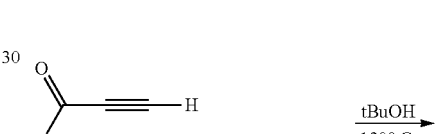

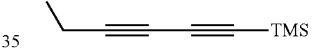

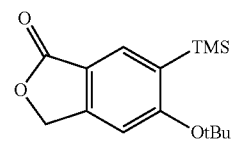

Spectral Data for the Product of Example 36

¹H NMR (500 MHz, CDCl₃): δ=7.89 (d, J=0.5 Hz, 1H), 6.98 (dt, J=0.5 and 1.0 Hz, 1H), 5.23 (d, J=1.0 Hz, 2H), 1.60 (s, 9H), and 0.29 (s, 9H). ¹³C NMR (125 MHz, CDCl₃): δ=171.2, 166.5, 150.5, 133.1, 133.0, 116.7, 106.4, 79.7, 69.1, 28.9, and -1.0 ppm. IR (neat): 2978, 2952, 1750, 1606, 1583, 1458, 1413, 1370, 1349, 1266, 1248, 1174, 1139, 1062, 1004, and 880 cm⁻¹. HR ESI-MS: $[C_{15}H_{22}O_3Si+Na]^+$ requires 301.1230. found 301.1181.

Example 37

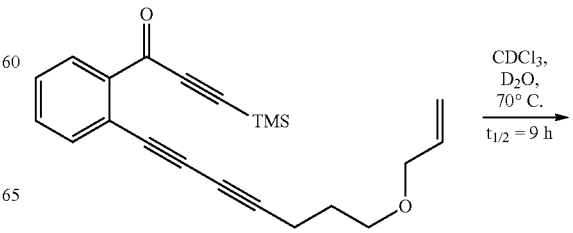

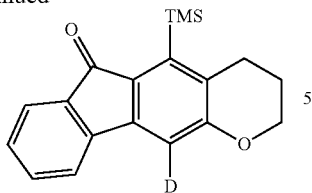

Spectral Data for the Product of Example 37

$^1$H NMR (500 MHz, CDCl$_3$): δ=7.55 (d, J=7.3 Hz, ArHCC=O), 7.39-7.44 (m, 2H), 7.25 (ddd, J=7.0, 7.0, 1.9 Hz, ArHCCCD), 4.21 (bt, J=5.1 Hz, CH$_2$OC), 2.88 (t, J=6.4 Hz, CH$_2$CH$_2$CH$_2$O), 2.01 (bp, J=6.4 Hz, CH$_2$CH$_2$CH$_2$O), and 0.43 [s, Si(CH$_3$)$_3$]. GC-MS t$_r$=12.34 min; m/z: 309, 294, 266, 208, 179, 175, 147 and 73.

Example 38

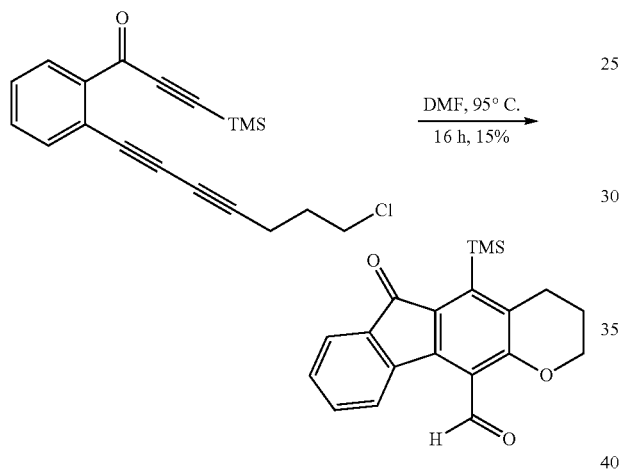

Spectral Data for the Product of Example 38

6-oxo-5-(trimethylsilyl)-2,3,4,6-tetrahydroindeno[2,1-g]chromene-11-carbaldehyde $^1$H NMR (500 MHz, CDCl$_3$): δ=10.61 (s, CHO), 8.23 (d, J=8.0 Hz, 1H), 7.58 (dd, J=7.5, 0.5 Hz, 1H), 7.45 (ddd, J=7.6, 7.6, 1.3 Hz, 1H), 4.32 (t, J=5.0 Hz, CH$_2$CH$_2$CH$_2$Cl), 2.93 (t, J=6.4 Hz, CH$_2$CH$_2$CH$_2$Cl), and 2.06 (tt, J=6.4, 5.0 Hz, CH$_2$CH$_2$CH$_2$Cl), and 0.44 [s, Si(CH$_3$)$_3$]. GC-MS t$_r$=13.60 min; m/z: 336, 321, 293, 265, 207, 178, 163, and 73.

Example 39

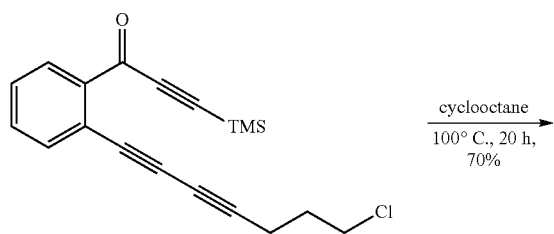

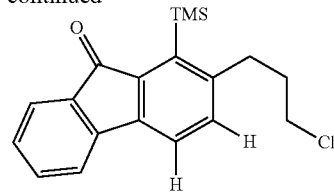

Spectral Data for the Product of Example 39

2-(3-Chloropropyl)-1-(trimethylsilyl)-9H-fluoren-9-one $^1$H NMR (500 MHz, CDCl$_3$): δ=7.58 (d, J=7.3 Hz, ArHCC=O), 7.44-7.46 (m, 3H, ArH), 7.23-7.27 (m, 2H, ArH), 3.55 (t, J=6.5 Hz, CH$_2$CH$_2$CH$_2$Cl), 2.95 (bt, J=7.6 Hz, CH$_2$CH$_2$CH$_2$Cl), 2.00 (bp, J=6.4 Hz, CH$_2$CH$_2$CH$_2$Cl), and 0.44 [s, Si(CH$_3$)$_3$]. HR ESI-MS: C$_{1-19}$H$_{21}$ClOSi [M+Na]$^+$ requires 351.0942. found 351.0969. GC-MS t$_r$=12.24 min; m/z: 328, 313, 277, 250, 235, 221, 203, 189, 165, 139, and 73.

Example 40

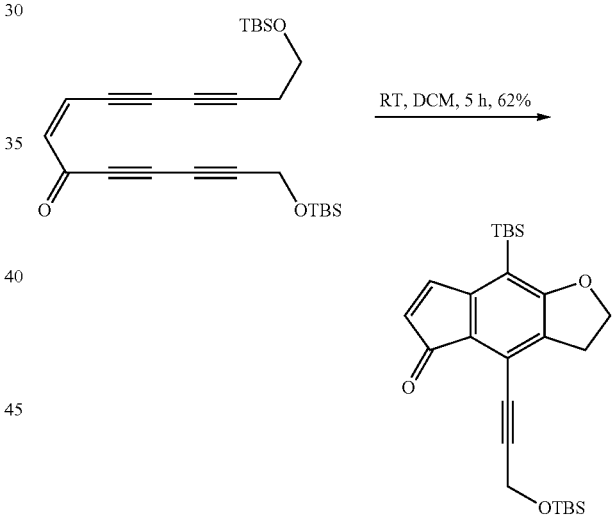

Spectral Data for the Product of Example 40

8-(tert-Butyldimethylsilyl)-4-(3-((tert-butyldimethylsilyl)oxy)prop-1-yn-1-yl)-2H-indeno[5,6-b]furan-5(3H)-one $^1$H NMR (500 MHz, CDCl$_3$): δ=7.49 (d, J=6.0 Hz, Ar—CH=), 5.83 (d, J=6.0 Hz, =CH—CO), 4.64 (s, OCH$_2$—C), 4.58 (t, J=9.0 Hz, CH$_2$CH$_2$O), 3.17 (t, J=9.0 Hz, C—CH$_2$), 0.94 (s, 9H), 0.90 (s, 9H), 0.36 (s, 6H), and 0.18 (s, 6H). $^{13}$C NMR (125 MHz, CDCl$_3$): δ=195.7 (C=O), 169.5, 154.1, 148.0, 127.5, 122.3, 117.5, 116.3, 97.0, 80.4, 79.5, 71.6 (OCH$_2$—C), 52.6 (OCH$_2$CH$_2$), 28.7 (OCH$_2$CH$_2$), 26.6 (C(CH$_3$)$_3$), 25.9 (C(CH$_3$)$_3$), 18.4 (C(CH$_3$)$_3$), 17.9 (C(CH$_3$)$_3$), −2.3 (Si(CH$_3$)$_2$), and −5.0 (Si(CH$_3$)$_2$).

Example 41

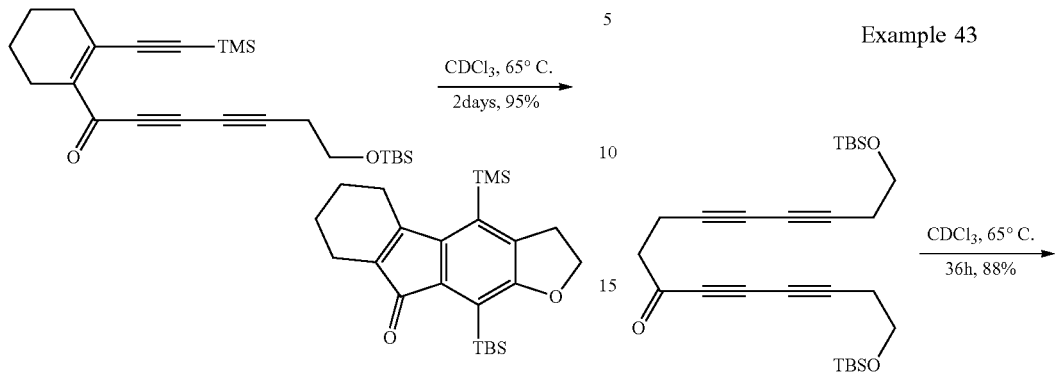

Spectral Data for the Product of Example 41

10-(tert-Butyldimethylsilyl)-4-(trimethylsilyl)-5,6,7,8-tetrahydro-2H-fluoreno[2,3-b]furan-9(3H)-one $^1$H NMR (500 MHz, CDCl$_3$): δ=4.37 (t, J=9.0 Hz, CH$_2$O), 3.15 (br t, J=9.0 Hz, ArCH$_2$), 2.58 [nfom, C=C(CH$_2$)—C=O], 2.22 (nfom, CH$_2$C=C—C=O), 1.74 (m, CH$_2$CH$_2$CH$_2$CH$_2$), 1.68 (m, CH$_2$CH$_2$CH$_2$CH$_2$), 0.94 (s, C(CH$_3$)$_3$), 0.42 (s, Si(CH$_3$)$_3$), and 0.34 (s, tBuSi(CH$_3$)$_2$). LC-MS: t$_r$=7.93 min; [M+H$_3$O]$^+$: 429.1

Example 42

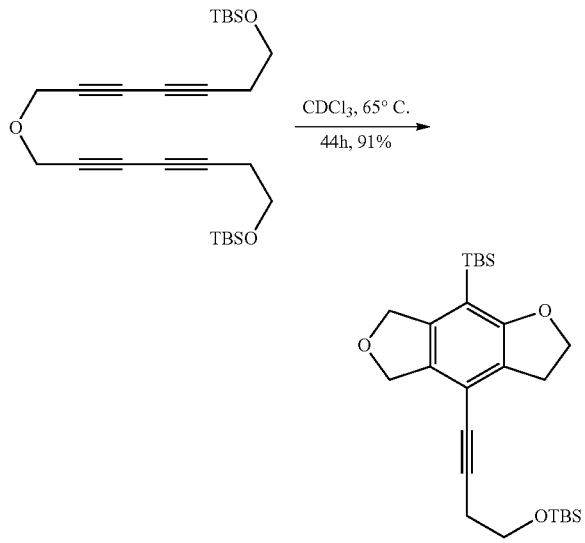

Spectral Data for the Product of Example 42 tert-butyl((4-(8-(tert-Butyldimethylsilyl)-2,3,5,7-tetrahydrobenzo[1,2-b:4,5-e]difuran-4-yl)but-3-yn-1-yl)oxy)dimethylsilane $^1$H NMR (500 MHz, CDCl$_3$): δ=5.06 (br s, 2H), 5.04 (br s, 2H), 4.52 (t, J=9.0 Hz, OCH$_2$CH$_2$—Ar), 3.80 (t, J=7.0 Hz, OCH$_2$CH$_2$—C), 3.16 (t, J=9.0H, OCH$_2$CH$_2$—Ar), 2.67 (t, J=7.0 Hz, OCH$_2$CH$_2$—C), 0.91 (s, C(CH$_3$)$_3$), 0.87 (s, C(CH$_3$)$_3$), 0.27 (s, tBuSi(CH$_3$)$_2$), 0.1 (s, tBuSi(CH$_3$)$_2$). LC-MS: t$_r$=10.51 min; [M+NH$_4$]$^+$: 476.2

Example 43

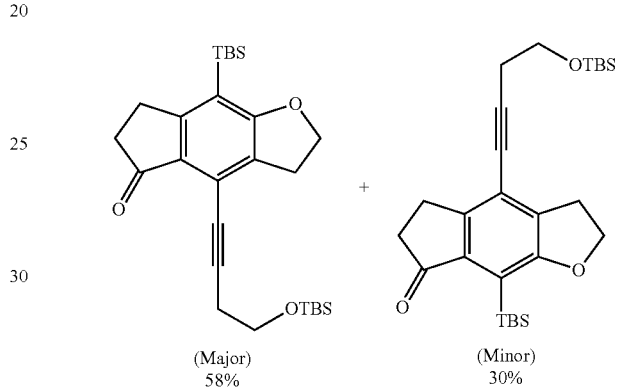

Spectral Data for the Products of Example 43

8-(tert-Butyldimethylsilyl)-4-(4-((tert-butyldimethylsilyl)oxy)but-1-yn-1-yl)-6,7-dihydro-2H-indeno[5,6-b]furan-5(3H)-one (Major)

$^1$H NMR (500 MHz, CDCl$_3$): δ=4.59 (t, J=8.5 Hz, OCH$_2$CH$_2$—Ar), 3.88 (t, J=7.5 Hz, OCH$_2$CH$_2$—C), 3.21 (t, J=8.5H, OCH$_2$CH$_2$—Ar), 3.02 (d, J=5.5 Hz) and 3.00 (d, J=5.5 Hz) [CH$_2$—C=O], 2.77 (t, J=7.5 Hz, OCH$_2$CH$_2$—C) 2.62 (d, J=5.5 Hz) and 2.61 (d, J=5.5 Hz) [CH$_2$CH$_2$—C=O], 0.90 (s, C(CH$_3$)$_3$), 0.89 (s, C(CH$_3$)$_3$), 0.36 (s, tBuSi(CH$_3$)$_2$), 0.09 (s, tBuSi(CH$_3$)$_2$). LC-MS: t$_r$=7.84 min; [M+H]$^+$: 471.1.

8-(tert-Butyldimethylsilyl)-4-(4-((tert-butyldimethylsilyl)oxy)but-1-yn-1-yl)-5,6-dihydro-2H-indeno[5,6-b]furan-7(3H)-one (Minor)

$^1$H NMR (500 MHz, CDCl$_3$): δ=4.52 (t, J=8.5 Hz, OCH$_2$CH$_2$—Ar), 3.83 (t, J=7.5 Hz, OCH$_2$CH$_2$—C), 3.24 (t, J=8.5H, OCH$_2$CH$_2$—Ar), 3.00 (d, J=6.0 Hz) and 2.99 (d, J=6.0 Hz) [CH$_2$—C=O], 2.71 (t, J=7.5 Hz, OCH$_2$CH$_2$—C) 2.64 (d, J=6.0 Hz) and 2.62 (d, J=6.0 Hz) [CH$_2$CH$_2$—C=O], 0.93 (s, C(CH$_3$)$_3$), 0.92 (s, C(CH$_3$)$_3$), 0.34 (s, tBuSi(CH$_3$)$_2$), 0.10 (s, tBuSi(CH$_3$)$_2$). LC-MS: t$_r$=6.65 min; [M+H]$^+$: 471.1

Example 44

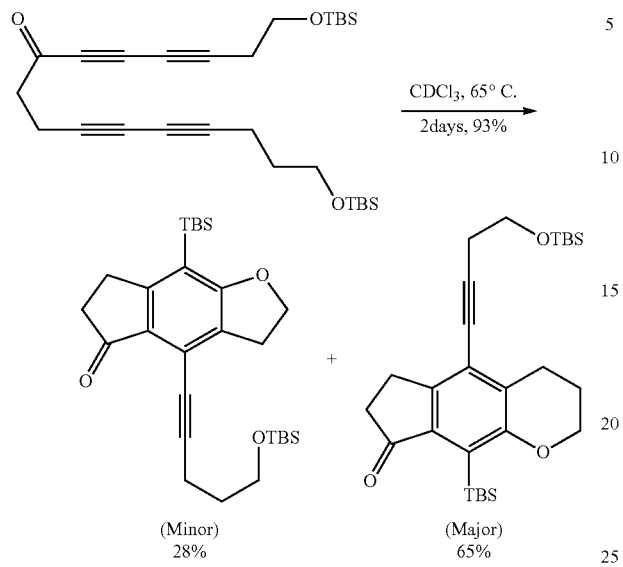

(Minor) 28%  (Major) 65%

Spectral Data for the Products of Example 44

9-(tert-Butyldimethylsilyl)-5-(4-((tert-butyldimethyl-silyl)oxy)but-1-yn-1-yl)-3,4,7,8-tetrahydrocyclopenta[g]chromen-6(2H)-one (Major)

$^1$H NMR (500 MHz, CDCl$_3$): δ=4.13 (d, J=5.5 Hz, ArOCH$_2$) and 4.12 (d, J=5.5 Hz, ArOCH$_2$), 3.90 (t, J=7.5 Hz, OCH$_2$CH$_2$—C), 3.01 (t, J=6.0 Hz) [CH$_2$—C=O], 2.89 (t, J=6.5 Hz, OCH$_2$CH$_2$CH$_2$—Ar), 2.69 (t, J=7.0 Hz, OCH$_2$CH$_2$—C), 2.59 (t, J=6.0 Hz) [CH$_2$CH$_2$—C=O], 1.98 (pentet, J=6.0 Hz, OCH$_2$CH$_2$CH$_2$—Ar), 0.91 (s, C(CH$_3$)$_3$), 0.90 (s, C(CH$_3$)$_3$), 0.35 (s, tBuSi(CH$_3$)$_2$), 0.09 (s, tBuSi(CH$_3$)$_2$).

8-(tert-Butyldimethylsilyl)-4-(5-((tert-butyldimethyl-silyl)oxy)pent-1-yn-1-yl)-5,6-dihydro-2H-indeno[5,6-b]furan-7(3H)-one (Minor)

$^1$H NMR (500 MHz, CDCl$_3$): δ=4.52 (t, J=8.5 Hz, OCH$_2$CH$_2$—Ar), 3.77 (t, J=6.5 Hz, OCH$_2$CH$_2$CH$_2$), 3.23 (t, J=8.5H, OCH$_2$CH$_2$—Ar), 3.00 (t, J=6.0 Hz) [CH$_2$—C=O], 2.80 (t, J=7.0 Hz, OCH$_2$CH$_2$CH$_2$—C), 2.63 (d, J=6.0 Hz) and 2.62 (d, J=6.0 Hz) [CH$_2$CH$_2$—C=O], 1.83 (pentet, J=6.0 Hz, CH$_2$CH$_2$CH$_2$—C), 0.92 (s, C(CH$_3$)$_3$), 0.89 (s, C(CH$_3$)$_3$), 0.34 (s, tBuSi(CH$_3$)$_2$), 0.08 (s, tBuSi(CH$_3$)$_2$).

Example 45

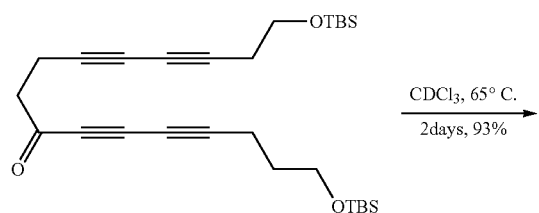

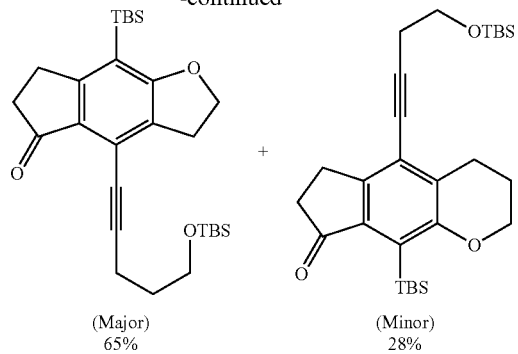

(Major) 65%  (Minor) 28%

Spectral Data for the Products of Example 45

8-(tert-Butyldimethylsilyl)-4-(5-((tert-butyldimethyl-silyl)oxy)pent-1-yn-1-yl)-6,7-dihydro-2H-indeno[5,6-b]furan-5(3H)-one (Major)

$^1$H NMR (500 MHz, CDCl$_3$): δ=4.59 (t, J=8.5 Hz, OCH$_2$CH$_2$—Ar), 3.80 (t, J=6.0 Hz, OCH$_2$CH$_2$CH$_2$), 3.21 (t, J=8.5H, OCH$_2$CH$_2$—Ar), 3.01 (d, J=6.0 Hz) and 3.00 (d, J=6.0 Hz) [CH$_2$—C=O], 2.62 (t, J=7.0 Hz, OCH$_2$CH$_2$CH$_2$—C), 2.61 (d, J=6.0 Hz) and 2.60 (d, J=6.0 Hz) [CH$_2$CH$_2$—C=O], 1.88 (pentet, J=6.0 Hz, CH$_2$CH$_2$CH$_2$—C), 0.90 (s, C(CH$_3$)$_3$), 0.89 (s, C(CH$_3$)$_3$), 0.36 (s, tBuSi(CH$_3$)$_2$), 0.07 (s, tBuSi(CH$_3$)$_2$).

9-(tert-Butyldimethylsilyl)-5-(4-((tert-butyldimethyl-silyl)oxy)but-1-yn-1-yl)-3,4,6,7-tetrahydrocyclopenta[g]chromen-8(2H)-one (Minor)

$^1$H NMR (500 MHz, CDCl$_3$): δ=4.08 (d, J=5.5 Hz, ArOCH$_2$) and 4.07 (d, J=5.5 Hz, ArOCH$_2$), 3.84 (t, J=7.0 Hz, OCH$_2$CH$_2$—C), 3.01 (d, J=6.0 Hz) and 3.00 (d, J=6.0 Hz) [CH$_2$—C=O], 2.94 (t, J=7.0 Hz, OCH$_2$CH$_2$CH$_2$—Ar), 2.73 (t, J=7.0 Hz, OCH$_2$CH$_2$—C), 2.61 (d, J=6.0 Hz) and 2.60 (d, J=6.0 Hz) [CH$_2$CH$_2$—C=O], 1.99 (pentet, J=6.5 Hz, OCH$_2$CH$_2$CH$_2$—Ar), 0.96 (s, C(CH$_3$)$_3$), 0.92 (s, C(CH$_3$)$_3$), 0.30 (s, tBuSi(CH$_3$)$_2$), 0.10 (s, tBuSi(CH$_3$)$_2$).

Example 46

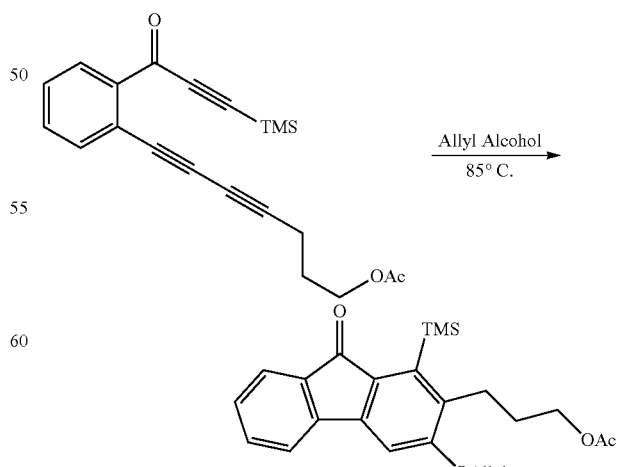

Spectral Data for Product of Example 46

$^1$H NMR (500 MHz, CDCl$_3$): δ=7.53 (ddd, J=7.5, 1.0, and 1.0 Hz, 1H), 7.42 (ddd, J=7.0, 7.0, and 1.0 Hz, 1H), 7.40 (ddd, J=6.0 and 1.0 Hz, 1H), 7.24 (ddd, J=7.0, 7.0, and 1.5 Hz, 1H), 6.99 (s, 1H), 6.10 (ddt, J=17.3, 10.6, and 4.9 Hz, 1H), 5.49 (ddt, J=17.0, 1.5, and 1.5 Hz, 1H), 5.35 (ddt, J=10.6, 1.5, and 1.5 Hz), 4.68 (ddd, J=4.5, 1.5, and 1.5 Hz, 2H), 4.12 (t, J=6.5 Hz, 2H), 2.91 (br t, J=8.5 Hz, 2H), 2.07 (s, 3H), 1.82 (m, 2H), and 0.45 (s, 9H).

Example 47

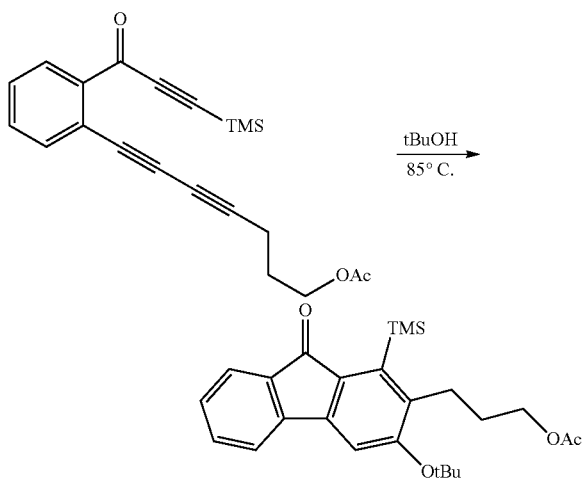

Spectral Data for Product of Example 47

$^1$H NMR (500 MHz, CDCl$_3$): δ=7.54 (d, J=7.5 Hz, 1H), 7.42 (dd, J=7.5 and 7.5 Hz, 1H), 7.38 (d, J=7.0 Hz, 1H), 7.24 (dd, J=7.0 and 7.0 Hz, 1H), 7.17 (s, 1H), 4.11 (t, J=6.5 Hz, 2H), 2.85 (br t, J=8.0 Hz, 2H), 2.06 (s, 3H), 1.78 (m, 2H), and 0.44 (s, 914). $^{13}$C NMR (125 MHz, CDCl$_3$): δ=194.2, 171.3, 159.5, 145.5, 143.51, 143.49, 140.7, 134.8, 134.0, 132.6, 128.9, 123.6, 119.0, 110.7, 80.0, 64.7, 30.8, 29.5, 26.8, 21.2, and 2.8 ppm. IR (neat): 2977, 2949, 1738, 1706, 1605, 1582, 1550, 1466, 1391, 1365, 1293, 1239, 1163, 1127, 1038, 998, and 948 cm$^{-1}$. HR ESI-MS: [C$_{25}$H$_{32}$O$_4$Si+Na]$^+$ requires 447.1962. found 447.1979.

Example 48

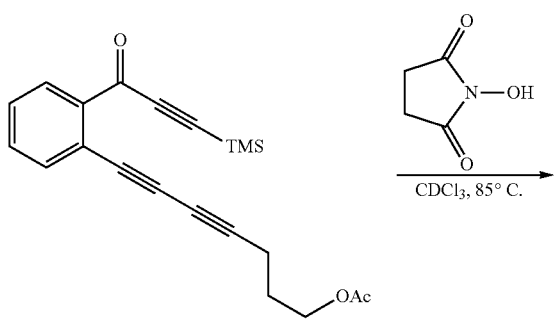

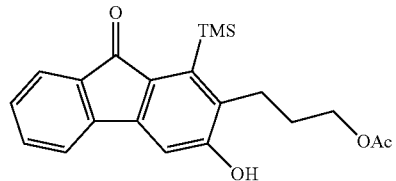

Spectral Data for Product of Example 48

$^1$H NMR (500 MHz, CDCl$_3$): δ=7.54 (d, J=7.0 Hz, 1H), 7.43 (dd, J=7.5 and 7.5 Hz, 1H), 7.37 (d, J=7.5 Hz, 1H), 7.26 (m, overlapped with CHCl$_3$ peak), 6.93 (s, 1H), 4.14 (t, J=6.5 Hz, 2H), 2.88 (br t, J=8.0 Hz, 2H), 2.09 (s, 3H), 1.89-1.82 (m, 2H), and 0.46 (s, 9H).

Example 49

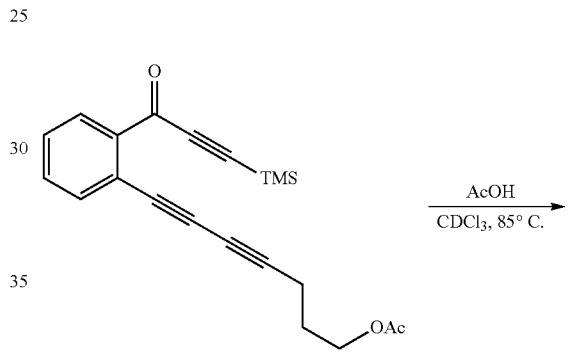

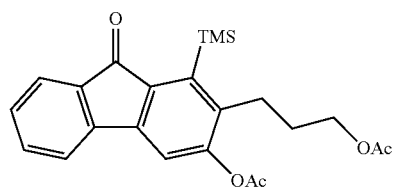

Spectral Data for Product of Example 49

$^1$H NMR (500 MHz, CDCl$_3$): δ=7.58 (d, J=7.5 Hz, 1H), 7.46 (ddd, J=7.5, 7.5 and 1.0 Hz, 1H), 7.41 (d, J=7.5 Hz, 1H), 7.28 (ddd, J=7.5, 7.5, and 1.0 Hz, 1H), 7.22 (s, 1H), 4.11 (t, J=6.5 Hz, 2H), 2.78 (br t, J=8.5 Hz, 2H), 2.39 (s, 3H), 2.08 (s, 3H), 1.82-1.75 (m, 2H), and 0.46 (s, 9H). $^{13}$C NMR (125 MHz, CDCl$_3$): δ=194.1, 171.0, 169.2, 153.0, 145.0, 142.2, 142.9, 139.9, 137.7, 134.5, 134.0, 129.2, 123.9, 119.8, 115.8, 64.0, 30.9, 26.2, 21.04, 20.98 and 2.6 ppm. IR (neat): 2949, 1759, 1739, 1713, 1605, 1591, 1467, 1387, 1366, 1295, 1243, 1201, 1159, 1118, 1039, 995, and 854 cm$^{-1}$. HR ESI-MS: [C$_{23}$H$_{26}$O$_5$Si+Na]$^+$ requires 433.1441. found 433.1436.

Example 50

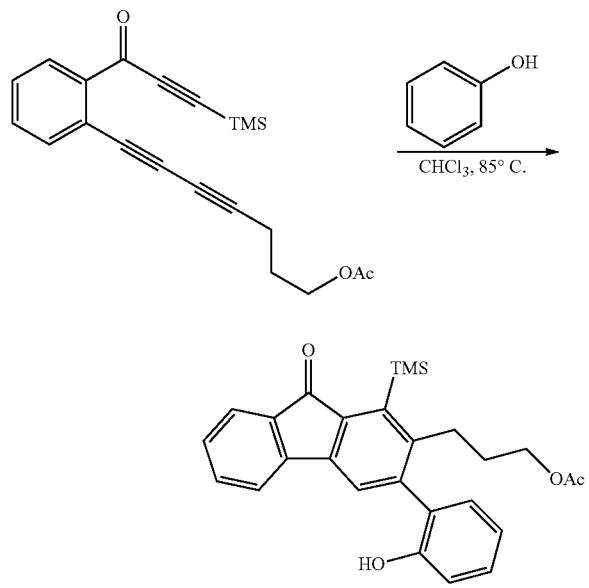

Spectral Data for Product of Example 50

$^1$H NMR (500 MHz, CDCl$_3$): δ=7.61 (ddd, J=7.5, 1.0 and 1.0 Hz, 1H), 7.46 (ddd, J=7.5, 7.5, and 1.0 Hz, 1H), 7.41 (ddd, J=7.5, 1.0, and 0.5 Hz, 1H), 7.40 (s, 1H), 7.32 (ddd, J=8.0, 8.0, and 1.0 Hz, 1H), 7.28 (ddd, J=7.5, 7.5, and 1.0 Hz, 1H), 7.15 (dd, 7.5 and 2.0 Hz, 1H), 7.03 (ddd, J=7.5, 7.5, and 1.0 Hz, 1H), 7.01 (dd, J=8.0 and 1.0 Hz, 1H), 4.84 (s, 1H), 3.82 (br t, J=6.0 Hz, 2H), 2.87 (ddd, J=14.0, 11.5, and 5.5 Hz, 1H), 2.65 (ddd, J=13.5, 11.0, and 5.5 Hz, 1H), 1.87 (s, 3H), 1.62 (m, 2H), and 0.49 (s, 9H). $^{13}$C NMR (125 MHz, CDCl$_3$): δ=195.1, 171.1, 152.2, 148.5, 143.60, 143.59, 143.4, 142.0, 140.7, 134.8, 134.0, 130.2, 129.7, 129.2, 128.4, 124.2, 123.9, 121.0, 119.8, 115.9, 63.8, 32.1, 29.8, 29.4, 21.0, and 2.9 ppm. IR (neat): 3440, 2951, 1736, 1710, 1606, 1590, 1541, 1464, 1448, 1386, 1363, 1247, 1185, 1040, and 979 cm$^{-1}$. HR ESI-MS: [C$_{27}$H$_{28}$O$_4$Si+Na]$^+$ requires 467.1649. found 467.1647

Example 51

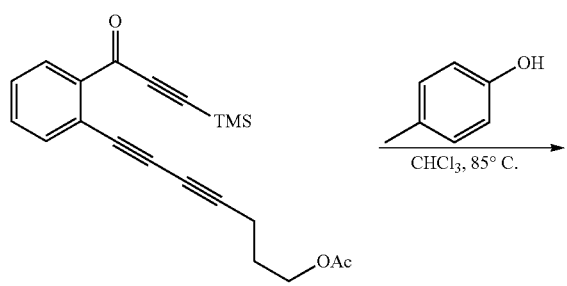

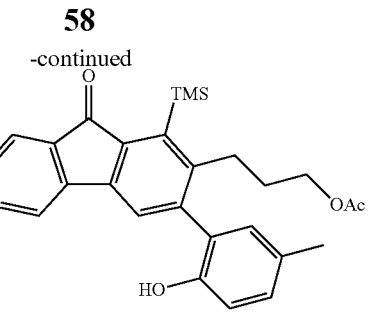

Spectral Data for Product of Example 51

$^1$H NMR (500 MHz, CDCl$_3$): δ=7.61 (ddd, J=7.5, 1.0 and 1.0 Hz, 1H), 7.45 (ddd, J=7.5, 7.5 and 1.0 Hz, 1H), 7.41 (ddd, J=7.0, 1.0, and 1.0 Hz, 1H), 7.38 (s, 1H), 7.28 (ddd, J=7.5, 7.5, and 1.0 Hz, 1H), 7.11 (dd, J=8.5 and 2.0 Hz, 1H), 6.95 (d, J=2.0 Hz, 1H), 6.90 (d, J=8.0 Hz, 1H), 4.69 (s, 1H), 3.84 (br t, J=6.5 Hz, 2H), 2.86 (ddd, J=13.5, 11.0, and 5.5 Hz, 1H), 2.67 (ddd, J=13.5, 11.0, and 5.5 Hz, 1H), 2.33 (dd, J=0.7 and 0.7 Hz, 3H), 1.88 (s, 3H), 1.70-1.56 (m, 2H), and 0.49 (s, 9H).

Example 52

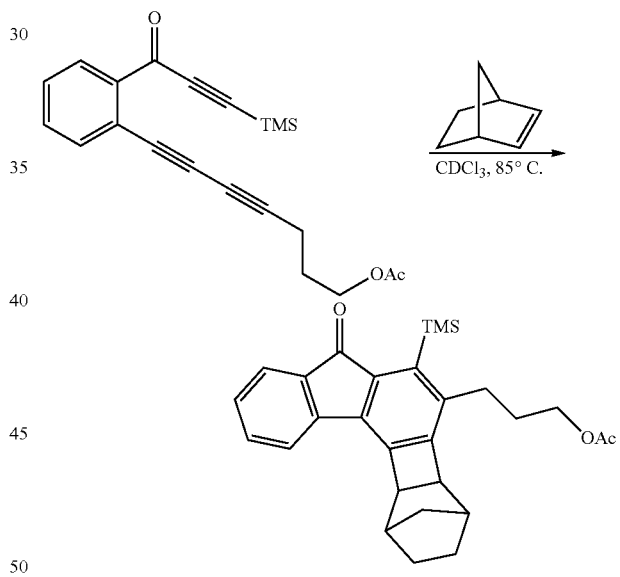

Spectral Data for Product of Example 52

$^1$H NMR (500 MHz, CDCl$_3$): δ=7.55 (ddd, J=7.5, 1.0 and 1.0 Hz, 1H), 7.41 (ddd, J=7.5, 7.5, and 1.0 Hz, 1H), 7.32 (ddd, J=7.0, 1.0, and 1.0 Hz, 1H), 7.22 (ddd, J=7.5, 7.5, and 1.0 Hz, 1H), 4.12 (br t, J=6.5 Hz, 2H), 3.31 (dd, J=4.0 and 1.0 Hz, 1H), 3.39 (dd, J=4.0 and 1.0 Hz, 1H), 2.71 (br t, J=8.0 Hz, 2H), 2.47 (br s, 1H), 2.37 (br s, 1H), 2.08 (s, 3H), 1.88-1.72 (m, 2H), 1.72-1.62 (m, 2H), 1.31-1.22 (m, 2H), 1.10 (br s, 2H), and 0.42 (s, 9H). $^{13}$C NMR (125 MHz, CDCl$_3$): δ=195.4, 171.2, 152.4, 143.1, 142.0, 140.7, 140.4, 140.3, 137.5, 134.6, 134.3, 128.6, 124.0, 121.5, 64.2, 52.1, 48.6, 36.5, 35.9, 32.7, 32.0, 28.0, 27.8, 27.7, 21.1, and 2.7 ppm. IR (neat): 2948, 2872, 1740, 1708, 1605, 1571, 1464, 1386, 1364, 1293, 1237, 1182, 1173, 1079, 1042, 997, 998, 950, and 917 cm$^{-1}$. HR ESI-MS: [C$_{28}$H$_{32}$O$_3$Si+Na]$^+$ requires 467.2013. found 467.2027

Example 53

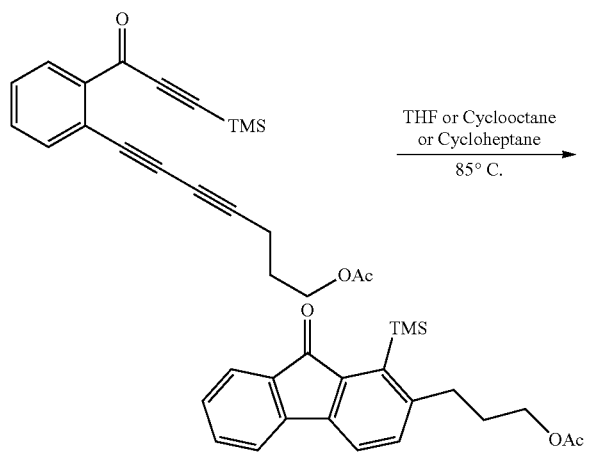

Spectral Data for Product of Example 53

$^1$H NMR (500 MHz, CD$_3$OD): δ=7.59 (br d, J=7.5 Hz, 1H), 7.58 (d, J=7.5, 1H), 7.53 (br dd, J=7.5 and 7.5 Hz, 1H), 7.51 (ddd, J=7.5, 7.5, and 1.0 Hz, 1H), 7.33 (d, J=8.0 Hz, 1H), 7.29 (ddd, J=7.5, 7.5, and 1.0 Hz, 1H), 4.10 (t, J=6.5 Hz, 2H), 2.88 (br t, J=8.0 Hz, 2H), 2.04 (s, 3H), 1.86 (m, 2H), and 0.43 (s, 9H). HR ESI-MS: [C$_{21}$H$_{24}$O$_3$Si+Na]$^+$ requires 375.1387. found 375.1386.

Example 54

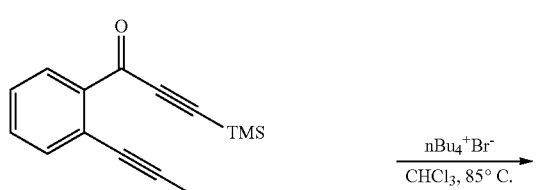

Spectral Data for Product of Example 54

Major Isomer
$^1$H NMR (500 MHz, CDCl$_3$): δ=7.76 (s, 1H), 7.60 (d, J=7.5 Hz, 1H), 7.48 (dd, J=7.0 and 7.0 Hz, 1H), 7.44 (d, J=7.5 Hz, 1H), 7.30 (dd, J=7.5 and 7.5 Hz), 4.17 (br t, J=6.5 Hz, 2H), 3.09 (br t, J=8.5 Hz, 2H), 2.08 (s, 3H), 1.90-1.80 (m, 2H), and 0.46 (s, 9H).

Minor Isomer
$^1$H NMR (500 MHz, CDCl$_3$): δ=8.32 (d, J=7.5 Hz, 1H), 7.63 (d, J=7.0 Hz, 1H), 7.55-7.48 (m, overlapped with major isomer peaks, 2H), 7.39 (s, 1H), 7.32 (dd, J=8.0 and 8.0 Hz, 1H), 4.12 (br t, J=6.5 Hz, 2H), 2.83 (br t, J=8.0 Hz, 2H), 2.08 (s, 3H), 1.90-1.80 (m, 2H), and 0.43 (s, 9H).

Example 55

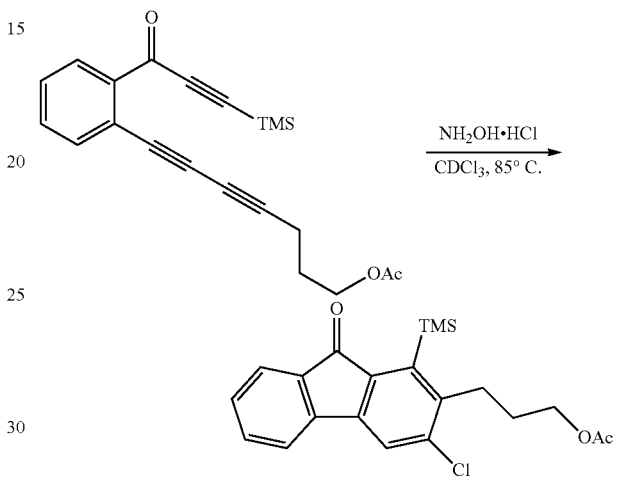

Spectral Data for Product of Example 55

$^1$H NMR (500 MHz, CDCl$_3$): δ=7.60 (ddd, J=7.5, 1.0 and 1.0 Hz, 1H), 7.55 (s, 1H), 7.48 (ddd, J=7.5, 7.5, and 1.0 Hz, 1H), 7.44 (ddd, J=7.5, 1.5, and 1.0 Hz, 1H), 7.30 (ddd, J=7.0, 7.0, and 1.0 Hz, 1H), 4.16 (t, J=6.5 Hz, 2H), 3.05 (br t, J=8.5 Hz, 2H), 2.08 (s, 3H), 1.88-1.82 (m, 2H), and 0.47 (s, 9H).

The starting polyalkynes used in the above reactions can be prepared using methods known in the field of organic

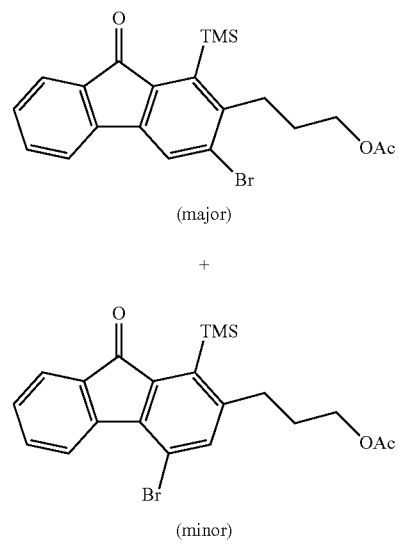

chemistry, or they can be prepared using methods similar to those described in Schemes 5-8 herein.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method comprising cyclizing a compound including three triple bonds, wherein two of the triple bonds are in a conjugated butadiyne subunit at a temperature below about 300° C. to provide a polycyclic compound having four carbon atoms from the two triple bonds that were in the conjugated butadiyne subunit present in a six-membered carbocyclic ring of the polycyclic compound.

2. A method comprising cyclizing a nonaromatic compound including three triple bonds, wherein two of the triple bonds are in a conjugated butadiyne subunit at a temperature below about 300° C. to provide a polycyclic compound having four carbon atoms from the two triple bonds that were in the conjugated butadiyne subunit present in a six-membered carbocyclic ring of the polycyclic compound.

3. The method of claim 1 further comprising contacting the polycyclic compound with a benzyne trapping reagent.

4. The method of claim 3 wherein the benzyne trapping reagent is a phenol, a furan, cyclooctane, cycloheptane, an alcohol, benzene, or a substituted benzene derivative.

5. The method of claim 3 wherein the benzyne trapping reagent is an aromatic agent, a formal hydrogen molecule ($H_2$) donor, an oxygen-based nucleophile of protic or aprotic nature, a sulfur containing nucleophile, a selenium-containing nucleophile, a phosphorous-containing nucleophile, a nitrogen-containing nucleophile, a halogen source, a metal halide salt, a hydrogen halide, an ammonium halide, a halosilane, an alkyl halide, or a pi-bond cycloaddend.

6. A polycyclic compound prepared according to the method of claim 3.

\* \* \* \* \*

UNITED STATES PATENT AND TRADEMARK OFFICE
CERTIFICATE OF CORRECTION

PATENT NO. : 9,505,789 B2
APPLICATION NO. : 13/756069
DATED : November 29, 2016
INVENTOR(S) : Thomas R. Hoye et al.

It is certified that error appears in the above-identified patent and that said Letters Patent is hereby corrected as shown below:

In the Specification

Column 1, Lines 11-14, STATEMENT OF GOVERNMENT RIGHTS, please delete "This invention was made with government support under and R01-CA76497 and R01-GM65597 awarded by the National Institutes of Health. The government has certain rights in the invention." and insert -- This invention was made with government support under CA076497 and GM065597 awarded by National Institutes of Health. The government has certain rights in the invention. -- therefor.

Signed and Sealed this
Nineteenth Day of June, 2018

Andrei Iancu
*Director of the United States Patent and Trademark Office*